(12) United States Patent  
Moore et al.

(10) Patent No.: US 8,097,406 B2  
(45) Date of Patent: Jan. 17, 2012

(54) ASSOCIATIONS OF SINGLE NUCLEOTIDE POLYMORPHISMS AND HAPLOTYPE WITH FEED INTAKE AND FEED EFFICIENCY IN BEEF CATTLE

(75) Inventors: Stephen Stewart Moore, Edmonton (CA); Esther Laura Sherman, Edmonton (CA); Joshua Donald Nkrumah, Edmonton (CA)

(73) Assignee: The Governors of the University of Alberta (CA)

( * ) Notice: Subject to any disclaimer, the term of this patent is extended or adjusted under 35 U.S.C. 154(b) by 419 days.

(21) Appl. No.: 11/969,795

(22) Filed: Jan. 4, 2008

(65) Prior Publication Data

US 2008/0177597 A1    Jul. 24, 2008

Related U.S. Application Data

(60) Provisional application No. 60/878,916, filed on Jan. 4, 2007.

(51) Int. Cl.
*C12Q 1/68* (2006.01)
*C12P 19/34* (2006.01)

(52) U.S. Cl. .......................................... 435/6; 435/91.2

(58) Field of Classification Search .................. None
See application file for complete search history.

(56) References Cited

U.S. PATENT DOCUMENTS

| | | | |
|---|---|---|---|
| 2005/0202484 A1 | 9/2005 | Moore | |
| 2008/0244763 A1* | 10/2008 | Moore | 800/21 |
| 2009/0117556 A1* | 5/2009 | Moore et al. | 435/6 |
| 2009/0275022 A1* | 11/2009 | Medrano et al. | 435/6 |

FOREIGN PATENT DOCUMENTS

WO    WO 2006 128116    11/2006

OTHER PUBLICATIONS

Sherman et al. (Animal Genetics 2008 VOI. 39 p. 225).*
Nkrumah et al. (Journal of Animal Science 2005 vol. 83 p. 20).*
Crews (Genet. Mol. Res 2004 VOI 4 p. 152-165).*
Rauw et al. (Journal of Animal Science 2006 vol. 84 p. 3404).*
Kolath et al. (J. Anim. Sci 2006 vol. 84 p. 1761).*
Halushka (Nature Genetics, 1999; 22:239-247).*
Robison et al. (Journal of Animal Science 1960 VOI. 19 p. 1013) teaches.*
Hegarty et al. (Journal of Animal Science 2007 vol. 85 p. 1479).*
Fishell et al. (Journal of Animal Science 1985 vol. 61 p. 151).*
Swanson et al. (Journal of Dairy Science 1967 VOI. 50 p. 244).*
Moore, Stephen et al., Bovine Genome Sequencing Program: Full Length cDNA Sequencing, 2005, Accession No. DN825517. [online], [retrieved on Jan. 23, 2009]. Retrieved from the Internet: URL:http://srs.ebi.ac.uk/srsbin/cgi-bin/wgetz?-e+[EMBL:DN825517]+-newld>. sequence on second page.

* cited by examiner

*Primary Examiner* — Katherine Salmon
(74) *Attorney, Agent, or Firm* — Judy Jarecki-Black; Chad Kitchen; Merial Limited

(57) ABSTRACT

The physiological regulation of intake, growth and energy partitioning in animals is under the control of multiple genes, which may be important candidates for unraveling the genetic variation in economically relevant traits in beef production. The present invention relates to the identification of single nucleotide polymorphisms (SNPs) and their haplotypes, across the bovine genome in genes encoding polypeptides associated with feed efficiency, and their associations with residual feed intake in beef production. The invention further encompasses methods and systems, including network-based processes, to manage the SNP data, haplotype data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

3 Claims, 15 Drawing Sheets

FIG. 1

BTA2_SNP25 – 118.4 cM - VSWAP1E32830A_scf01
[SEQ ID NO. 1]
GGGGCTCTGTGGCAGGTCGGGTGAAATGAGTGCGGCTGAGACTCCACGCCCTGCAGCACGGG
GCTCTGTAGCAGGTCAGGACTCTGGAGTTGATCCCCCA[G/A]CACCGCCACGTGCACCCCCTTT
CCTCAGGTCATCGACAAGAGCAAGCGAGACCCCTCGGAAGAGATTGAAATTCTTCTGCGGTACG
GGCAGCACCCCAAC

FIG. 2

BTA2_SNP24 – 117.4 cM - BES8_Contig556_1629
[SEQ ID NO. 2]
GGCTCTCAGCTCTCCCATGTGTCATTTCTAACTTCCCATAAAAGCCCTTGGCAGAGCGGATTTCA
GTCGCTCGAGGGGGATATTCAGGTTCAAGAAATAG[A/C]AAGCTTATACGTAAATACTTGTAAATA
AAAAAGCTTATAAACACATTAAATGAACCCAATGGACAGAGCCCCTTTCCTGCCCTGGGAAGGCA
GACGCAGT

FIG. 3

BTA2_SNP26 – 118.5 cM - SCAFFOLD225703_8029
[SEQ ID NO. 3]
CAGTGATGCAGTGGAGTTTCTGCTTTGGAGTCATTCCTGTCTACATTTGAATTCTTACTCAATATA
TTACTAAGCTGTCTGACTTTTGCCAACACACCTC[G/T]CGAGCCTCAGTATCCTCATCTGTCAGAT
AGGGGCATAATGCCTACTTCATGATATTGTGGTGAGAATTACATGAGATAACAGATGAATCCTGG
ATTATCC

FIG. 4

BTA5_SNP36 – 91.6 cM - BES7_Contig480_1179
[SEQ ID NO. 4]
ATTTTAAACTACTTTGTTTAGAAAAGAGTGGTTAGGGTTTTGTAGCACTTCCTTTGTTCATTTTTGC
CTCACTAATAACACCTAGACTCATACTTTGGCC[C/T]CAGCAGTACAGAGGATACAGGTATTGTTT
TCTTTAAAAAAAAAAACAAAAAACAAAAAACAGTCCCATTTGAAAGAGAAACAATGGTGGTATTGC
TCTTT

FIG. 5

BTA5_SNP35 – 91.3 - SCAFFOLD175093_3639
[SEQ ID NO. 5]
AAGTGAGACCAGAGCGCGCCCGACGATGCGGTGGCTGTAGTGGTGAAGCTCCCAAGTTGAGCT
TTTCTCGGCGGTTGTTGGGCAGCTTTGCAGATGGGAA[G/A]TTATCAGCCTCTTAGCAGCCCTGA
GCTGCCGTGGCGCGGGGATTTGGGGAGGAAAGGACCGCAGGCAGAAGCTCTCTCCCGACCTG
CAGCCTTGACTGTT

FIG. 6

BTA5_SNP37 – 91.8 cM - BES3_Contig341_801
[SEQ ID NO. 6]
AATCACTTTCAGTAATTATCTGAATAGATCTTATGGATAACTTGCTGCCGCTTCTACATCAGCAGG
TGTTGTTTCATCTTGCACTTTTGTGTTAATGGGG[A/G]TATTTTCTTTTTGAAAGCCTTATGAATCA
AACTCTCCTAGCTTCCAGCTTTAAATTAGAATTAAAGAGTTAGGACCATGCTCTGGGTCAGGCCT
TGGCTT

FIG. 7

BTA10 SNP31 – 113.9 cM - SCAFFOLD155540_1585
[SEQ ID NO. 7]
TTTGTGTGTCTGTGTGTGTTGTTTGTTTCATTTTAGTTAAAAGGAGAAATGTTATTTTCTATATT
GATGAGCTTTGGTTTGAGCAAGGAAGAGATGAA[C/G]GTTCCTAGGAGCTGTGGGTCTTCAATAA
TGGATACAGTCGACAGGAGTACTTTCTCTGCCTGAGTAACAGAGAACCCATGATGACTGAGTAGT
TCAGAAA

FIG. 8

BTA10 SNP32 – 115.1 cM- VSWAP1D42164A_scf04
[SEQ ID NO. 8]
TAAGGTCAATGGAAACTGCCTGTGCTATGTAGGGGCAGTACTACCCAGGGGATGAGAAATCAGC
CCTGGAGTCAGATGTATCCAGTTTTAATTCCAGCTC[T/A]GTTCTCTACTAGGTGAGCAAACTTGG
GCAAGCTACTATAGTCACTGAACCTCAACTTCCCTCTCTTGAAAATGGGTATAAAAACTGTACCTG
CTAGGGGA

FIG. 9

BTA20 SNP50 – 42.7cM - VSWAP1D54566A_scf
[SEQ ID NO. 9]
ACCAATTGGCATTAACAAGTGTGATAGGTATTTGAAAAATTGTTGGCAAAACAACTTTCTTGGAAG
ACAGAACAAAAGAATTAGGAGGTTTAGAAGTCAG[G/A]CAACTTCTAATATCTTATACCATTGACA
GTGATTTGTTCCTGTCATAGCTCTTCTCTGACCTGTTAGTGAAGGACAAAATTCTAAAAAAATGTT
TAGTCA

FIG. 10

BTA20 SNP49 – 42.7 - SCAFFOLD115711_487
[SEQ ID NO. 10]
TTTCCAAGCTGTGATAGCTTATTATTCTGATTCCCTATGTACCAACTATTCTGCTTGATGGTCTCTT
TGTAATTCTTCCCTTTTGCAGTATTTTGGTTTT[A/G]AATTTCTCTTCTTAGAAGTTTGGGTGAACTC
TCTGCTGGATGGCAAACTCCTTGAATGTAGGGGTTTGCTTTAATGCTTCCTTAATTAGACCAGAG
CTTG

FIG. 11

BTA29 SNP18 - 57.4 cM - 3104-421-R
[SEQ ID NO. 11]
CCGCTACAACCTGGCAGCCCTGGCCTTGGCCCCCCGGAGCCGGCTGGACGCCTTCGATTACGA
CTGGTACAACGTCTCTGATCAGGTGGGCATTCGACACATCTGCCGCCTCCCCAGTAGCTGTGGC
TCCTGGCCCCAGCTGGCCTGGGTCCGGTCTGGGGGCCGCATTGGCATGACTGCAGATCGGCA
CAGCCCCTGCCTCCCACAGGCGGACCTGGTGAACGACCTGGGGAACAAAGGCTACCTGGTGT
TTGGCCTCATCCTCTTTGTGTGGGAGCTGCTGCCCACCACCCTGCTGGTGGGCTTCTTCCGGGT
ACATCGGCCCCGCAGGACCTGGTGAGGCCAGTGGAGAGGGCGGCACTGGCGGTCCCTGG
GCTGGGTTCTGGGGGTGTGGGAGGCCAGTGGGGGGCAGAAG[G/A]AAGCATCAATGGTGGCTC
CCTTCCCTAGAGCACCAGCCGCATCCTCAACATNNNTTTTNNTNNNTGGNGTTTTTNNTGTGTTG
TAATTTGGGGTTGGAAAGGATGGTTAATTTTTGTGAAAAGACTTATTCTCAGGGGTGTTATCATA
GCGTTTGAAACCACAAGATTGATTGTGGGCTCAACCTTGAAAAGGTTACGGTTTTTTCCAAAAAAT
GAACTTGGCCACCAAATCCGTGAGCAAAAGGGGGGCCCACCTTTTGGCATGACATAAAGGAGGC
ATTTTGGGGGGGAACCTTTTGTCCAAAAGGGGGGAGCCCCCAAACGAATTCAAAGAACTGCCCC
CTGGGTTTTTAAGTGGTAACCGGATCCAAAACAATTGACCTCCTTCCCGGGGGGCGGAGAAAAA
CAGTAGGCCACAATAACCCTGGGGGGGGATTGCCACATGGGGAAATGGAGATTTGAGGGGGCC
CTTTTGCTAATGAGGAAACCTGGCACTCCCACAAGTTAACCTATAATGATAGGGGTAGGGAGGCA
AGAGGGATTTTAAG

FIG. 12

BTA29 SNP20 – 57.6 cM - BES4_Contig495_1744
[SEQ ID NO. 12]
CAAGAAGATGCAGTTGAAGGAGGAAGCCAGACAGCCCTTCCCCAGCACAGCAAGAGAGGTTCG
GACAATGGACTTATCTAGAGAAAAAGGAGGAGGTCAG[C/T]GGGATCTTGGGAGAGGGGGTTGA
GAAGTTGGGTCACTTCTGGGGATGTGGCCAAGGACGAGGGACCAAGGTGCTCATGGGTGCTCA
CCCTTGGGTACCAC

FIG. 13

BTA29 SNP21 – 57.6 cM – SCAFFOLD58698_4308
[SEQ ID NO. 13]
TCCCAGGTCAAGCAAAGGCCATGGCACAGGATCTTCAACTCTAAATGCTTGTTGAATTAAAACGA
GTTGAAGGAAGTGCAGAGGGAGCAGCTGTAGGCAG[G/A]TCAAAAGAGGTTTGGGAGAAGCAAG
GAAATATGAATGTTGAGGTTGGTGACACTGATTAGGAGCATTCATAGGAATTCAGAACCTTCTAG
ACCATCCCCC

FIG. 14 (1/3)

BTA2

SNP25 – 118.4 cM – VSWAP1E32830A_scf01
GGGGCTCTGTGGCAGGTCGGGTGAAATGAGTGCGGCTGAGACTCCACGCCCTGCAGCACGGG
GCTCTGTAGCAGGTCAGGACTCTGGAGTTGATCCCCCA[G/A]CACCGCCACGTGCACCCCCTTT
CCTCAGGTCATCGACAAGAGCAAGCGAGACCCCTCGGAAGAGATTGAAATTCTTCTGCGGTACG
GGCAGCACCCCAAC

HAP23 contains:

SNP24 – 117.4 cM – BES8_Contig556_1629
GGCTCTCAGCTCTCCCATGTGTCATTTCTAACTTCCCATAAAAGCCCTTGGCAGAGCGGATTTCA
GTCGCTCGAGGGGGATATTCAGGTTCAAGAAATAG[A/C]AAGCTTATACGTAAATACTTGTAAATA
AAAAAGCTTATAAACACATTAAATGAACCCAATGGACAGAGCCCCTTTCCTGCCCTGGGAAGGCA
GACGCAGT

SNP25 – 118.4 cM – VSWAP1E32830A_scf01
See above

HAP24 contains:

SNP25 – 118.4 cM – VSWAP1E32830A_scf01
See above

SNP26 – 118.5 cM – SCAFFOLD225703_8029
CAGTGATGCAGTGGAGTTTCTGCTTTGGAGTCATTCCTGTCTACATTTGAATTCTTACTCAATATA
TTACTAAGCTGTCTGACTTTTGCCAACACACCTC[G/T]CGAGCCTCAGTATCCTCATCTGTCAGAT
AGGGGCATAATGCCTACTTCATGATATTGTGGTGAGAATTACATGAGATAACAGATGAATCCTGG
ATTATCC

BTA5

SNP36 – 91.6 cM – BES7_Contig480_1179
ATTTTAAACTACTTTGTTTAGAAAAGAGTGGTTAGGGTTTTGTAGCACTTCCTTTGTTCATTTTTGC
CTCACTAATAACACCTAGACTCATACTTTGGCC[C/T]CAGCAGTACAGAGGATACAGGTATTGTTT
TCTTTAAAAAAAAAAACAAAAAACAAAAAACAGTCCCATTTGAAAGAGAAACAATGGTGGTATTGC
TCTTT

HAP34 contains:

SNP35 – 91.3 - SCAFFOLD175093_3639
AAGTGAGACCAGAGCGCGCCCGACGATGCGGTGGCTGTAGTGGTGAAGCTCCCAAGTTGAGCT
TTTCTCGGCGGTTGTTGGGCAGCTTTGCAGATGGGAA[G/A]TTATCAGCCTCTTAGCAGCCCTGA
GCTGCCGTGGCGCGGGGATTTGGGGAGGAAAGGACCGCAGGCAGAAGCTCTCTCCCGACCTG
CAGCCTTGACTGTT

SNP36 – 91.6 cM – BES7_Contig480_1179
See above

HAP35 contains:
SNP36 – 91.6 cM – BES7_Contig480_1179
See above
SNP37 – 91.8 cM – BES3_Contig341_801
AATCACTTTCAGTAATTATCTGAATAGATCTTATGGATAACTTGCTGCCGCTTCTACATCAGCAGG
TGTTGTTTCATCTTGCACTTTTGTGTTAATGGGG[A/G]TATTTTCTTTTTGAAAGCCTTATGAATCA
AACTCTCCTAGCTTCCAGCTTTAAATTAGAATTAAAGAGTTAGGACCATGCTCTGGGTCAGGCCT
TGGCTT

FIG. 14 (2/3)

BTA10

HAP30 contains:

SNP31 – 113.9 cM - SCAFFOLD155540_1585
TTTGTGTGTCTGTGTGTGTTGTTTGTTTCATTTTAGTTAAAAGGAGAAATGTTATTTTCTATATT
GATGAGCTTTGGTTTGAGCAAGGAAGAGATGAA[C/G]GTTCCTAGGAGCTGTGGGTCTTCAATAA
TGGATACAGTCGACAGGAGTACTTTCTCTGCCTGAGTAACAGAGAACCCATGATGACTGAGTAGT
TCAGAAA

SNP32 – 115.1 cM- VSWAP1D42164A_scf04
TAAGGTCAATGGAAACTGCCTGTGCTATGTAGGGGCAGTACTACCCAGGGGATGAGAAATCAGC
CCTGGAGTCAGATGTATCCAGTTTTAATTCCAGCTC[T/A]GTTCTCTACTAGGTGAGCAAACTTGG
GCAAGCTACTATAGTCACTGAACCTCAACTTCCCTCTCTTGAAAATGGGTATAAAAACTGTACCTG
CTAGGGGA

BTA20

SNP50 – 42.7cM - VSWAP1D54566A_scf
ACCAATTGGCATTAACAAGTGTGATAGGTATTTGAAAAATTGTTGGCAAAACAACTTTCTTGGAAG
ACAGAACAAAAGAATTAGGAGGTTTAGAAGTCAG[G/A]CAACTTCTAATATCTTATACCATTGACA
GTGATTTGTTCCTGTCATAGCTCTTCTCTGACCTGTTAGTGAAGGACAAAATTCTAAAAAAATGTT
TAGTCA

HAP18 contains:

SNP49 – 42.7 - SCAFFOLD115711_487
TTTCCAAGCTGTGATAGCTTATTATTCTGATTCCCTATGTACCAACTATTCTGCTTGATGGTCTCTT
TGTAATTCTTCCCTTTTGCAGTATTTTGGTTTT[A/G]AATTTCTCTTCTTAGAAGTTTGGGTGAACTC
TCTGCTGGATGGCAAACTCCTTGAATGTAGGGGTTTGCTTTAATGCTTCCTTAATTAGACCAGAG
CTTG

SNP50 – 42.7cM - VSWAP1D54566A_scf
See above

BTA 29

SNP18 - 57.4 cM - 3104-421-R
CCGCTACAACCTGGCAGCCCTGGCCTTGGCCCCCGGAGCCGGCTGGACGCCTTCGATTACGA
CTGGTACAACGTCTCTGATCAGGTGGGCATTCGACACATCTGCCGCCTCCCCAGTAGCTGTGGC
TCCTGGCCCCAGCTGGCCTGGGTCCGGTCTGGGGGCCGCATTGGCATGACTGCAGATCGGCA
CAGCCCCTGCCTCCCACAGGCGGACCTGGTGAACGACCTGGGGAACAAAGGCTACCTGGTGT
TTGGCCTCATCCTCTTTGTGTGGGAGCTGCTGCCCACCACCCTGCTGGTGGGCTTCTTCCGGGT
ACATCGGCCCCGCAGGACCTGGTGAGGGCCAGTGGAGAGGGGCGGCACTGGCGGTCCCTGG
GCTGGGTTCTGGGGGTGTGGGAGGCCAGTGGGGGGCAGAAG[G/A]AAGCATCAATGGTGGCTC
CCTTCCCTAGAGCACCAGCCGCATCCTCAACATNNNTTTTNNTNNNTGGNGTTTTTNNTGTGTTG
TAATTTGGGGTTGGAAAGGATGGTTAATTTTTTGTGAAAAGACTTATTCTCAGGGGTGTTATCATA
GCGTTTGAAACCACAAGATTGATTGTGGGCTCAACCTTGAAAAGGTTACGGTTTTTTCCAAAAAAT
GAACTTGGCCACCAAATCCGTGAGCAAAAGGGGGGCCCACCTTTTGGCATGACATAAAGGAGGC
ATTTTGGGGGGGAACCTTTTGTCCAAAAGGGGGAGCCCCCAAACGAATTCAAAGAACTGCCCC
CTGGGTTTTTAAGTGGTAACCGGATCCAAAACAATTGACCTCCTTCCCGGGGGCGGAGAAAAA
CAGTAGGCCACAATAACCCTGGGGGGGGATTGCCACATGGGGAAATGGAGATTTGAGGGGGCC
CTTTTGCTAATGAGGAAACCTGGCACTCCCACAAGTTAACCTATAATGATAGGGGTAGGGAGGCA
AGAGGGATTTTAAG

FIG. 14 (3/3)

<u>HAP 28 contains:</u>

SNP20 – 57.6 cM - BES4_Contig495_1744
CAAGAAGATGCAGTTGAAGGAGGAAGCCAGACAGCCCTTCCCCAGCACAGCAAGAGAGGTTCG
GACAATGGACTTATCTAGAGAAAAAGGAGGAGGTCAG[C/T]GGGATCTTGGGAGAGGGGGTTGA
GAAGTTGGGTCACTTCTGGGGATGTGGCCAAGGACGAGGGACCAAGGTGCTCATGGGTGCTCA
CCCTTGGGTACCAC

SNP21 – 57.6 cM – SCAFFOLD58698_4308
TCCCAGGTCAAGCAAAGGCCATGGCACAGGATCTTCAACTCTAAATGCTTGTTGAATTAAAACGA
GTTGAAGGAAGTGCAGAGGGAGCAGCTGTAGGCAG[G/A]TCAAAAGAGGTTTGGGAGAAGCAAG
GAAATATGAATGTTGAGGTTGGTGACACTGATTAGGAGCATTCATAGGAATTCAGAACCTTCTAG
ACCATCCCCC

US 8,097,406 B2

ASSOCIATIONS OF SINGLE NUCLEOTIDE POLYMORPHISMS AND HAPLOTYPE WITH FEED INTAKE AND FEED EFFICIENCY IN BEEF CATTLE

INCORPORATION BY REFERENCE

This application claims benefit of U.S. provisional patent application Ser. No. 60/878,916 filed Jan. 4, 2007.

The foregoing applications, and all documents cited therein or during their prosecution ("appln cited documents") and all documents cited or referenced in the appln cited documents, and all documents cited or referenced herein ("herein cited documents"), together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to methods and systems of identification and management of beef cattle. More specifically, the invention relates to methods and systems relating to identification of single nucleotide polymorphisms (SNPs) and haplotypes associated with feed intake and feed efficiency The invention further relates to methods and systems, including network-based processes, to manage the SNP data and other data relating to specific animals and herds of animals, veterinary care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Animals account for almost 20 percent of the world's food consumption, and animal-based food products are a major source of revenue throughout the world. In the United States alone, beef production is the fourth largest manufacturing industry and accounts for nearly 25 percent of the farm sector cash receipts and seven percent of supermarket sales each year. Feeding costs account for most of the total variable costs in beef production, Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-inheritable and need to be applied differently in every production system.

There is a need for methods that allow relatively easy and more efficient selection and breeding of farm animals that have an advantage for an inheritable trait of enhanced feed intake and feed efficiency. The economic significance of the use of genetic markers that are associated with specific economically important traits (especially traits with low heritability) in livestock through marker-assisted selection cannot therefore be over-emphasized.

The physiological regulation of intake, growth and energy partitioning in animals is under the control of multiple genes, which may be important candidates for unraveling the genetic variation in economically relevant traits (ERT) in beef production. Polymorphisms in these candidate genes that show association with specific ERT are useful quantitative trait nucleotides for marker-assisted selection and management. Haplotypes that consist of a series of single nucleotide polymorphisms (SNPs) in a segment of DNA that are inherited together can also be used to evaluate such associations.

Polymorphisms in candidate genes that show association with specific ERT may be useful quantitative trait nucleotides for marker-assisted selection. It remains advantageous to provide further SNPs, so that a more accurate prediction can be made of the feed intake and feed efficiency phenotypes of an animal, and also enable a business method that provides for increased residual feed intake in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to associations between SNPs and haplotypes of SNPs on five bovine chromosomes with measures of feed intake, residual feed intake (RFI) and feed conversion ratio in beef cattle.

The invention encompasses a method for sub-grouping animals according to genotype wherein the animals of each sub-group have similar polymorphisms in RFI-associated genes that may comprise determining the genotype of each animal to be sub-grouped by determining the presence of single nucleotide polymorphisms in the RFI-associated genes, and segregating individual animals into sub-groups wherein each animal in a sub-group has similar polymorphisms in the RFI-associated genes.

The invention also encompasses a method for sub-grouping animals according to genotype wherein the animals of each sub-group have a similar genotype in the RFI-associated genes that may comprise determining the genotype of each animal to be sub-grouped by determining the presence of single nucleotide polymorphism(s) of interest in the RFI-associated genes, and segregating individual animals into sub-groups depending on whether the animals have, or do not have, the single nucleotide polymorphism(s) of interest in the RFI-associated genes.

The single nucleotide polymorphism(s) of interest may be selected from the group consisting of the follow:

SNPs (Bovine Chromosome 2)
1. a G to A nucleotide substitution at the 118.4 centi Morgan (cM) position (SNP25; phenotypic Residual Feed Intake [pRFI])
2. a G to A nucleotide substitution at the 118.4 cM position (SNP25; genetic Residual Feed Intake [gRFI]).
3. a G to A nucleotide substitution at the 118.4 cM position (SNP25; Feed Conversion Ratio [FCR]).
4. a G to A nucleotide substitution at the 118.4 cM position (SNP25; Partial Efficiency of Growth [DMI]).

SNPs Forming the Haplotypes (Bovine Chromosome 2)
1. Haplotype 23 (HAP23) 117.9 mid-point cM position pRFI
2. HAP23 117.9 mid-point cM position gRFI.

3. HAP23 117.9 mid-point cM position FCR
4. HAP23 117.9 mid-point cM position PEG
5. HAP24 118.45 mid-point cM position gRFI
6. HAP24 118.45 mid-point cM position pRFI
7. HAP24 118.45 mid-point cM position FCR
8. HAP24 118.45 mid-point cM position PEG SNPs (Bovine Chromosome 5)
1. a C to T nucleotide substitution at the 96.1 cM position (SNP36 pRFI)
2. a C to T nucleotide substitution at the 96.1 cM position (SNP36, gRFI).
3. a C to T nucleotide substitution at the 96.1 cM position (SNP36, Dry Matter Intake [DMI])
4. a C to T nucleotide substitution at the 96.1 cM position (SNP36, Partial Efficiency of Growth [peg])

SNPs Forming the Haplotypes (Bovine Chromosome 5)
1. HAP34 91.45 mid-point cM position pRFI
2. HAP34 91.45 mid-point cM position gRFI
3. HAP34 91.45 mid-point cM position FCR
4. HAP35 91.7 mid-point cM position gRFI
5. HAP35 91.7 mid-point cM position pRFI
6. HAP35 91.7 mid-point cM position PEG SNPs Forming the Haplotypes (Bovine Chromosome 10)
1. HAP30 114.5 mid-point cM position pRFI
2. HAP30 114.5 mid-point cM position gRFI.
3. HAP30 114.5 mid-point cM position DMI
4. HAP30 114.5 mid-point cM position FCR
5. HAP30 114.5 mid-point cM position PEG SNPs (Bovine Chromosome 20)
1. an A to G nucleotide substitution at the 42.7 cM position (SNP50; pRFI)
2. an A to G nucleotide substitution at the 42.7 cM position (SNP50; gRFI)
3. an A to G nucleotide substitution at the 42.7 cM position (SNP50; DMI)
4. an A to G nucleotide substitution at the 42.7 cM position (SNP50; FCR)
5. an A to G nucleotide substitution at the 42.7 cM position (SNP50; PEG)

SNPs Forming the Haplotypes (Bovine Chromosome 20)
1. HAP18 42.7 cM mid-point position pRFI
2. HAP18 42.7 cM mid-point position gRFI
3. HAP18 42.7 cM mid-point position PEG SNPs (Bovine Chromosome 29)
1. an A to G nucleotide substitution at the 57.4 cM position (SNP18; pRFI)
2. an A to G nucleotide substitution at the 57.4 cM position (SNP18; gRFI)
3. an A to G nucleotide substitution at the 57.4 cM position (SNP18; PEG)

SNPs Forming the Haplotypes (Bovine Chromosome 29)
1. HAP28 57.6 mid-point cM position pRFI
2. HAP28 57.6 mid-point cM position gRFI
3. HAP28 57.6 mid-point cM position DMI
4. HAP28 57.6 mid-point cM position PEG The invention further relates to a method for sub-grouping animals according to genotype wherein the animals of each sub-group have similar haplotypes in the RFI-associated genes that may comprise determining the genotype of each animal to be sub-grouped by determining the presence of any of the above SNPs, and segregating individual animals into sub-groups depending on whether the animals have, or do not have, any of the above SNPs in the RFI-associated genes.

The invention also relates to method for identifying an animal having a desirable phenotype as compared to the general population of animals of that species, which may comprise determining the presence of single nucleotide polymorphisms in the RFI-associated genes of the animal, wherein the presence of the SNP's are indicative of a desirable phenotype.

In an advantageous embodiment, the animal may be a bovine. In another advantageous embodiment, the RFI-associated genes may be bovine RFI-associated genes.

The invention also encompasses computer-assisted methods and systems for improving the production efficiency for livestock having marketable feed efficiency and feed intake using multiple data, and in particular the genotype of the animals as it relates to RFI-associated SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes and haplotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the RFI-associated genes related to feed intake and feed efficiency and associating those data with other data about the animal or its herd, and maintaining those data in ways that are accessible. Another aspect of the invention encompasses a computer-assisted method for predicting which livestock animals possess a biological difference in RFI, and which may include the steps of using a computer system, e.g., a programmed computer comprising a processor, a data storage system, an input device and an output device, the steps of: (a) inputting into the programmed computer through the input device data that includes a genotype of an animal as it relates to any one of the RFI-associated SNPs described herein, (b) correlating feed intake and feed efficiency predicted by the RFI-associated genotypes using the processor and the data storage system and (c) outputting to the output device the feed intake and feed efficiency correlated to the RFI-associated genotypes, thereby predicting which livestock animals possess enhance feed efficiency and feed intake.

Yet another aspect of the invention relates to a method of doing business for managing livestock comprising providing to a user a computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein such physical characteristics as feed intake, feed efficiencies, and growth genotypes are associated with the RFI genotype and haplotypes.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which:

FIG. 1 depicts the nucleic acid sequence of BTA2, SNP25 at 118.4 centi Morgan (SEQ ID NO: 1)

FIG. 2 depicts the nucleic acid sequence of BTA2, SNP24 at 117.4 cM (SEQ ID NO: 2)

FIG. 3 depicts the nucleic acid sequence of BTA2, SNP26 at 188.5 cM (SEQ ID NO: 3)

FIG. 4 depicts the nucleic acid sequence of BTA5, SNP36 at 91.6 cM (SEQ ID NO: 4)

FIG. 5 depicts the nucleic acid sequence of BTA5, SNP35 at 91.3 cM (SEQ ID NO: 5)

FIG. 6 depicts the nucleic acid sequence of BTA5, SNP37 at 91.8 cM (SEQ ID NO: 6)

FIG. 7 depicts the nucleic acid sequence of BTA10, SNP31 at 113.9 cM (SEQ ID NO: 7)

FIG. 8 depicts the nucleic acid sequence of BTA10, SNP32 at 115.1 cM (SEQ ID NO: 8)

FIG. 9 depicts the nucleic acid sequence of BTA20, SNP50 at 42.7 cM (SEQ ID NO: 9)

FIG. 10 depicts the nucleic acid sequence of BTA20, SNP49 at 42.7 cM (SEQ ID NO: 10)

FIG. 11 depicts the nucleic acid sequence of BTA29, SNP18 at 57.4 cM (SEQ ID NO: 11)

FIG. 12 depicts the nucleic acid sequence of BTA29, SNP20 at 57.6 cM (SEQ ID NO: 12)

FIG. 13 depicts the nucleic acid sequence of BTA29, SNP21 at 57.6 cM (SEQ ID NO: 13)

FIG. 14 is a summary of the described RFI SNP sequences (SEQ ID NOS 1-13 respectively in order of appearance) and locations of polymorphisms.

DETAILED DESCRIPTION

Figure 15:
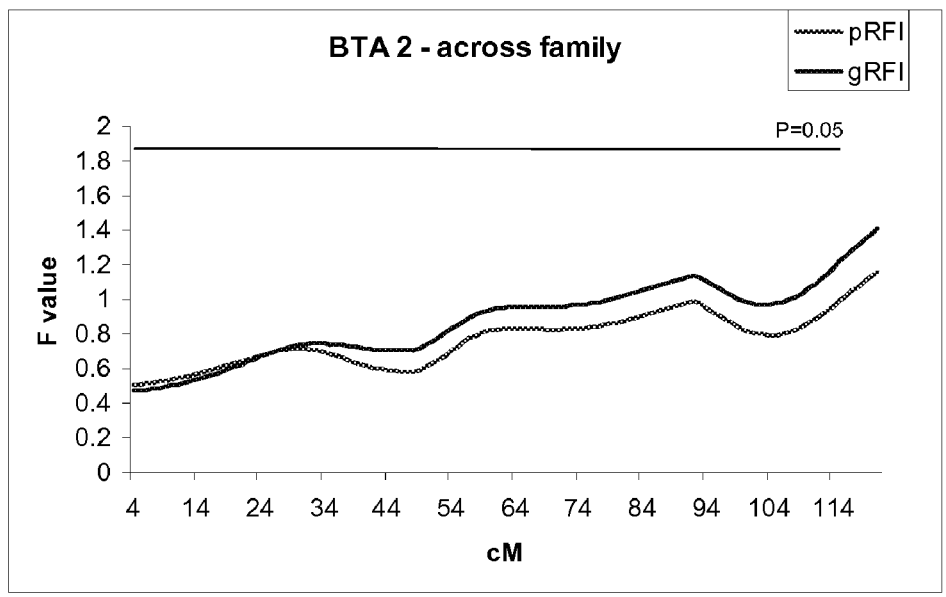
Figure 16:
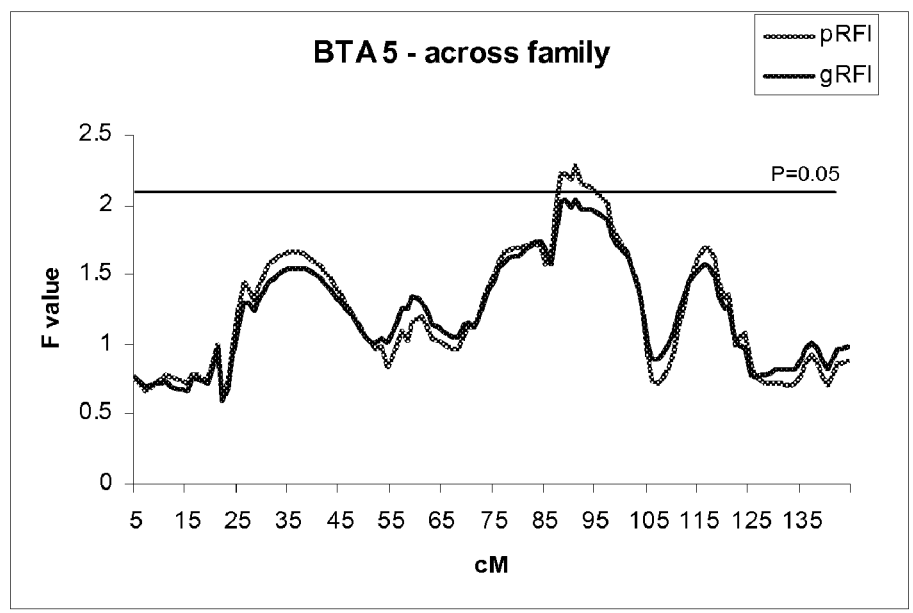
FIG. 16 illustrates the fine mapping analysis of Quantiative Trait Loci identified on Bovine chromosome 5.
Figure 17:
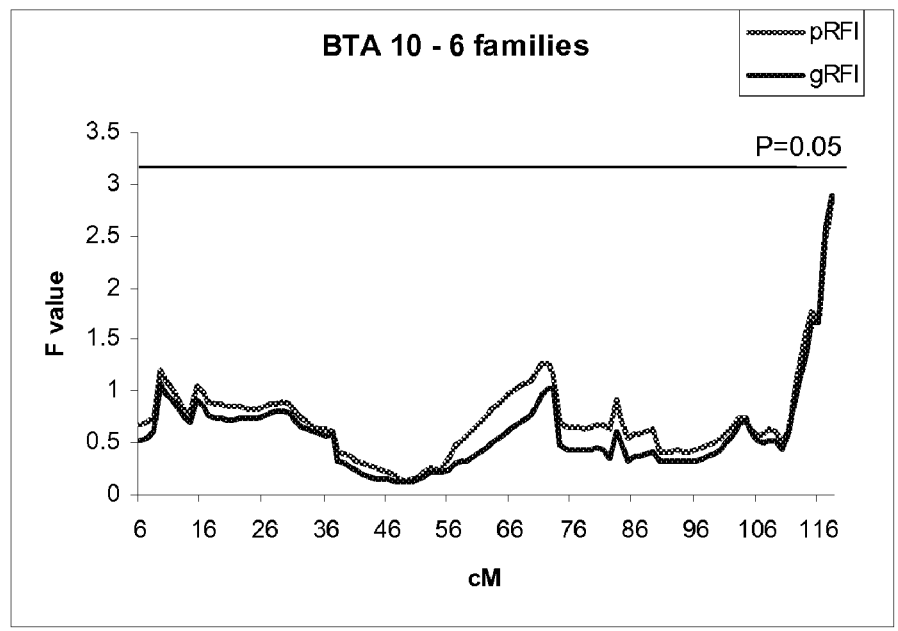
FIG. 17 illustrates the fine mapping analysis of Quantiative Trait Loci identified on Bovine chromosome 10.
Figure 18:
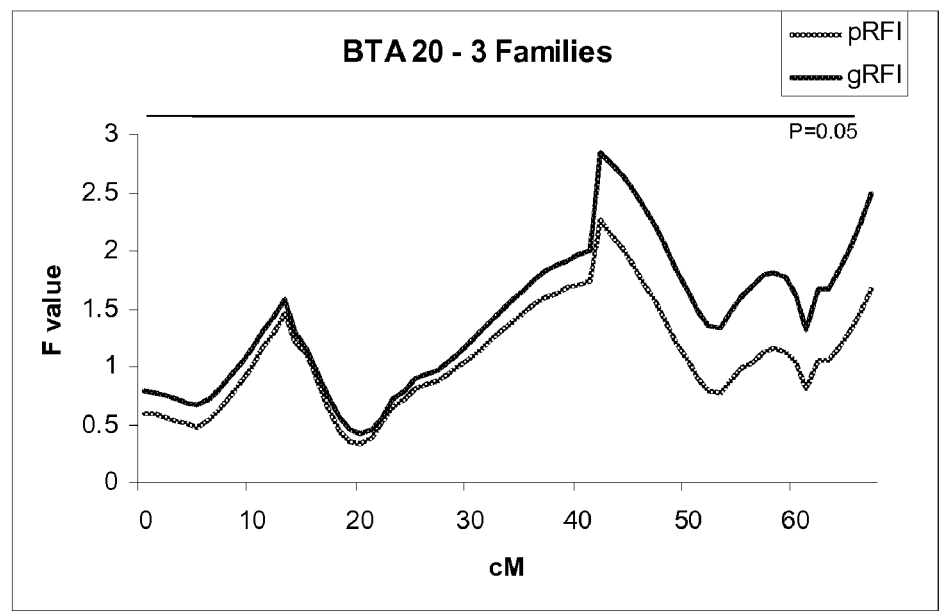
FIG. 18 illustrates the fine mapping analysis of Quantiative Trait Loci identified on Bovine chromosome 20.
Figure 19:
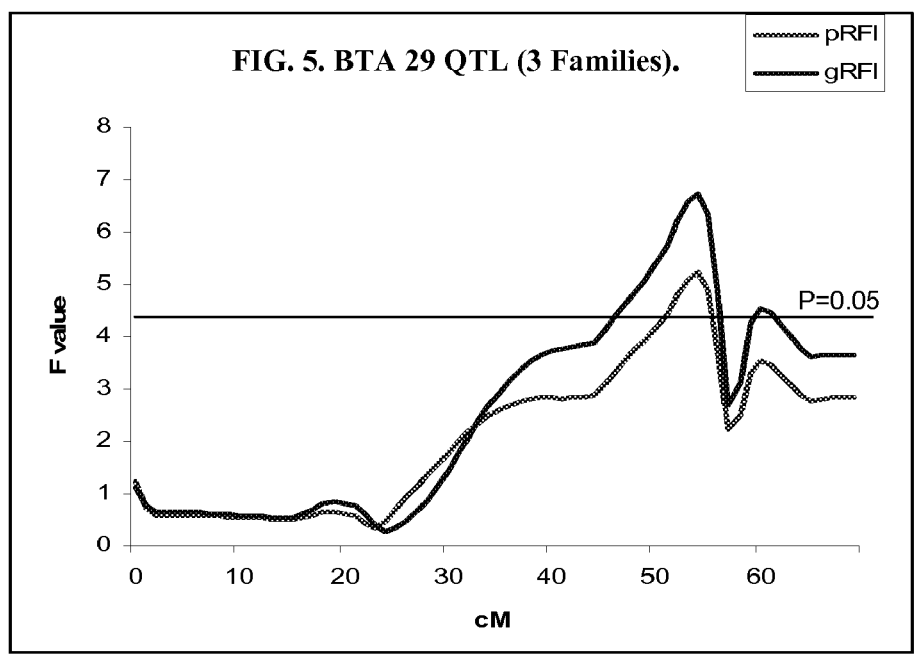
FIG. 19 illustrates the fine mapping analysis of Quantiative Trait Loci identified on Bovine chromosome 26.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule. "DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); QB replicase amplification (QBRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype." By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as Thermus aquaticus. Examples of thermostable polymerases include Taq, Tth, Pfu, Vent, deep vent, UITma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand.

Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene(s) of interest is bovine RFI, the bovine RFI nucleotide sequence can be selected from, but is not limited to, the sequences corresponding to SEQ ID NO 1 through SEQ ID NO 13, or fragments thereof or a region of the bovine genome that comprises said sequence(s).

The present invention, therefore, provides isolated nucleic acids that may specifically hybridize to the nucleotide sequence corresponding to GenBank Accession No. NW_930497.1 or the complement thereof, and which comprises the polymorphic site corresponding to nucleotide positions −1220, −1212 or −995.

The single nucleotide polymorphism(s) of interest may be selected from the group comprising the nucleotide substitutions defined in SEQ ID NO 1 through SEQ ID NO 13 (FIG. 1 through FIG. 13).

The SNPs advantageous in the present invention are associated with certain economically valuable and heritable traits relating to meat quality in bovines. Therefore, it is an object of the present invention to determine the genotype of a given animal of interest as defined by the nucleotide substitutions defined in SEQ ID NO 1 through SEQ ID NO 13 (FIG. 1 through FIG. 13) according to the present invention. It is also contemplated that the genotype of the animal(s) may be defined by additional SNPs within the RFI genes or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with SNPs located within the RFI genes. The methods further allow, by computer-assisted methods of the invention, to correlate SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid.

Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the RFI genes, advantageously of the region encompassing an RFI SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with an RFI gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref} - N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in an RFI gene which are unique to an RFI gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3$H, $^{125}$I, $^{35}$S, $^{14}$C, $^{32}$P, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and Mac-Beath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the RFI gene polymorphic sites associated with economically relevant traits of growth, feed intake, efficiency and/or carcass merit, would lead to a breed, line, or population having higher numbers of offspring with economically relevant traits of growth, feed intake, efficiency and carcass merit. Thus, the RFI-associated SNPs of the present invention can be used as a selection tool.

Desirable phenotypes include, but are not limited to, feed intake, growth rate, body weight, carcass merit and composition, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs,> Ch), ribeye area (REA, in²), ribeye area per hundred weight HCW (REA/cwt HCW, in²/100 lb hot carcass weight (HCW) and subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the RFI-associated genes of the present invention. Other SNPs that may be included in panels of SNPs include, but not limited to, SNPs found in the calpastatin gene, FGF8 gene, GHR gene, TFAM gene, GHR gene, FABP4 gene, ghrelin gene, leptin gene, NPY gene, ob gene, UASMS1 gene, UASMS2 gene, UASMS3 gene and/or the UCP2 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a desired body condition by identifying the presence or absence of one or more gene polymorphisms correlated with meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or sub-grouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are RFI-associated sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the RFI-associated sequences described herein.

Another embodiment of the invention is an oligonucleotide that specifically hybridizes under high stringency conditions to any one of the polymorphic sites of the RFI-associated genes, wherein the oligonucleotide is between about 18 nucleotides and about 50 nucleotides.

In another embodiment of the invention, the oligonucleotide comprises a central nucleotide specifically hybridizing with a RFI-associated genes polymorphic site of the portion of the nucleic acid molecule.

Another aspect of the invention is a method of identifying a RFI-associated polymorphisms in a nucleic acid sample comprising isolating a nucleic acid molecule encoding RFI-associated genes or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by polymorphisms in the RFI-associated genes.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the RFI-associated gene or a portion thereof that contains the polymorphism. In other embodiments of the invention, the amplification may include the step of selecting a forward and a reverse sequence primer capable of amplifying a region of the RFI-associated gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising an RFI-associated genotype of an animal, (b) correlating growth, feed intake, efficiency or carcass merit quality predicted by the RFI-associated genotype using the processor and the data storage system and (c) outputting to the output device the meat quality correlated to the RFI-associated genotype, thereby predicting which livestock animals possess a particular growth level, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

This Example provides DNA loci, genetic polymorphisms and significant associations with carcass merit in beef cattle for bovine residual feed intake (RFI-associated) genes.

The physiological regulation of feed intake, growth and energy partitioning in animals are under the control of multiple genes, which are candidates for unraveling the genetic variation in economically relevant traits (ERT) in beef production. Polymorphisms that show association with a specific ERT may be useful quantitative trait nucleotides for marker-assisted selection and management. Haplotypes which consist of a series of single nucleotide polymorphisms (SNP) in a segment of DNA that are inherited together can also be used to evaluate such associations. In example, we show associations between SNPs and haplotypes of SNPs on five bovine chromosomes with measures of feed intake, residual feed intake and feed conversion ratio in beef cattle.

Feed efficiency is an important ERT in beef cattle. Net feed efficiency or residual feed intake may be expressed either as genetic (gRFI, computed from genetic regression) or phenotypic (PRFI, computed from phenotypic regression). RFI represents an animal's inate ability to efficiently utilize feed energy for maintenance and gain (Koch 1963). Animals that eat less than expected and therefore have a lower RFI are more efficient than animals that eat more than expected and have a higher RFI. Positive aspects for using RFI as a measure of feed efficiency is that it is phenotypically independent of the production traits used to measure it. Therefore, it may indicate variation in basic metabolic processes in the animals that determine efficiency (Archer et al. 1999). Evidence suggests RFI is heritable in cattle (Arthur, Archer et al. 2001) and other species such as mice (Hughes, 1997) and poultry (Luiting et al. 1991). This suggests that genetic variation exists for RFI and therefore the identification of polymorphisms affecting this trait is possible (Archer, 1999). Other measures of feed efficiency include feed conversion ratio (FCR) which is the the ratio of daily dry matter intake (DMI) to average daily gain (ADG). Partial efficiency of growth (PEG) is another measure of feed efficiency and is calculated as the ratio of ADG to the difference between average DMI and expected DMI for maintenance where epexted DMI for maintenance is calculated according to NRC (1996).

Locating polymorphisms affecting quantitative traits such as RFI involves mapping the genetic effect to a particular location on a bovine chromosome (BTA) using statistical analysis. These locations are known as quantitative trait loci (QTL). The whole bovine genome was analyzed for QTL for residual feed intake (RFI) using 455 markers across the 29 chromosomes with and average spacing of 6.18 cM. This study identified RFI QTL on BTA 2, 5, 10, 20 and 29. More SNPs were added to these chromosomes in order to fine map and narrow the QTL regions. An average of 108 SNP per chromosome at approximately every 1 cM was used.

The experimental animals used to collect the phenotypes in this study were Continental×British hybrid beef steers sired by Angus, Charolais or University of Alberta Hybrid bulls. Feed intake, growth and carcass data were collected over two years under feedlot conditions at the University of Alberta's Kinsella beef cattle research station. Genomic DNA was extracted from blood samples using a standard high salt phenol/chloroform extraction method. Genotyping of the SNP was carried out using the Illumina GoldenGate assay on the BeadStation system (Illumina Inc., San Diego, Calif.), which allows the simultaneous genotyping of 1,536 SNPs using 250 ng of genomic DNA per sample.

QTL from the fine mapping analysis were identified and are shown in FIGS. 15 to 19. Several SNPs were then chosen within these QTL regions and were tested for associations with RFI, FCR, PEG and daily DMI using General Linear Mixed Model in SAS. The statistical analyses model included fixed effects of the SNP, contemporary test group (six levels), breed of sire (three levels), a linear covariate of age of animal on test, and random effects of sire and dam of animal. Allele substitution effects were also estimated using the SNP as a covariate in the same model. These SNP were also used to form haplotypes containing two SNP at a time across each QTL region of interest. These haplotypes were analyzed for allele substitution effects and associations using the same methods as the SNP analysis. Significant associations and allele substitution effects (P<0.05) were found for several SNPs and Haplotypes and are shown in Tables 1 through 15. These tables also contain the allele and haplotype frequencies and positions of the SNPs or haplotypes on the chromosomes. FIGS. 1-13 contain the specific SNP sequence information (SEQ ID NOs 1 through 13), and FIG. 14 reiterates the sequence information and name of each SNP as well as the SNPs that form the haplotypes.

TABLE 1

BTA2 SNP allele substitution effects and ls means.

| SNP25-pRFI | | | | Genotype | | |
|---|---|---|---|---|---|---|
| cM | 118.4 | | | GG | AG | AA |
| Allele Sub. Effect | −0.217 | Freq | | 0.02 | 0.29 | 0.69 |
| SE | 0.077 | LS Mean | | 0.684 | 0.055 | −0.084 |
| pvalue | 0.005 | SE | | 0.237 | 0.077 | 0.055 |
| SNP25-gRFI | | | | Genotype | | |
| cM | 118.4 | | | GG | AG | AA |
| Allele Sub. Effect | −0.246 | Freq | | 0.02 | 0.29 | 0.69 |
| SE | 0.074 | LS Mean | | 0.605 | −0.068 | −0.234 |
| pvalue | 0.001 | SE | | 0.240 | 0.074 | 0.048 |
| SNP25-FCR | | | | Genotype | | |
| cM | 118.4 | | | GG | AG | AA |
| Allele Sub. Effect | −0.260 | Freq | | 0.02 | 0.29 | 0.69 |
| SE | 0.106 | LS Mean | | 8.058 | 7.373 | 7.196 |
| pvalue | 0.015 | SE | | 0.323 | 0.114 | 0.088 |
| SNP25-PEG | | | | Genotype | | |
| cM | 118.4 | | | GG | AG | AA |
| Allele Sub. Effect | 0.011 | Freq | | 0.02 | 0.29 | 0.69 |
| SE | 0.004 | LS Mean | | 0.255 | 0.284 | 0.292 |
| pvalue | 0.008 | SE | | 0.014 | 0.004 | 0.0023 |

TABLE 2

BTA 2 Haplotype effects and associations.

| HAP23 | Haplotype Overall | | | Individual Haplotypes | | | |
|---|---|---|---|---|---|---|---|
| pRFI | mid point cM | 117.9 | | A-G | A-A | C-A | C-G |
| | P value | 0.031 | Freq | 0.13 | 0.50 | 0.33 | 0.04 |
| | | | Effect | −0.269 | −0.427 | −0.438 | 0 |
| | | | SE | 0.246 | 0.205 | 0.223 | |
| | | | P value | 0.274 | 0.038 | 0.050 | |
| HAP23 | Haplotype Overall | | | Individual Haplotypes | | | |
| gRFI | mid point cM | 117.9 | | A-G | A-A | C-A | C-G |
| | P value | 0.008 | Freq | 0.13 | 0.50 | 0.33 | 0.04 |
| | | | Effect | −0.280 | −0.468 | −0.474 | 0 |
| | | | SE | 0.249 | 0.208 | 0.227 | |
| | | | P value | 0.260 | 0.025 | 0.037 | |

TABLE 2-continued

BTA 2 Haplotype effects and associations.

| HAP23 | Haplotype Overall | | | Individual Haplotypes | | | |
|---|---|---|---|---|---|---|---|
| FCR | mid point cM | 117.9 | | A-G | A-A | C-A | C-G |
| | P value | 0.048 | Freq | 0.13 | 0.50 | 0.33 | 0.04 |
| | | | Effect | −0.376 | −0.577 | −0.537 | 0 |
| | | | SE | 0.331 | 0.276 | 0.299 | |
| | | | P value | 0.256 | 0.037 | 0.073 | |

| HAP23 | Haplotype Overall | | | Individual Haplotypes | | | |
|---|---|---|---|---|---|---|---|
| PEG | mid point cM | 117.9 | | A-G | A-A | C-A | C-G |
| | P value | 0.047 | Freq | 0.13 | 0.50 | 0.33 | 0.04 |
| | | | Effect | 0.012 | 0.021 | 0.022 | 0 |
| | | | SE | 0.014 | 0.012 | 0.013 | |
| | | | P value | 0.384 | 0.074 | 0.092 | |

| HAP24 | Haplotype Overall | | | Individual Haplotypes | | | |
|---|---|---|---|---|---|---|---|
| pRFI | mid point cM | 118.45 | | G-T | G-G | A-T | A-G |
| | P value | 0.047 | Freq | 0.06 | 0.11 | 0.38 | 0.45 |
| | | | Effect | 0.253 | 0.218 | 0.029 | 0 |
| | | | SE | 0.146 | 0.118 | 0.068 | |
| | | | P value | 0.274 | 0.038 | 0.050 | |

| HAP24 | Haplotype Overall | | | Individual Haplotypes | | | |
|---|---|---|---|---|---|---|---|
| gRFI | mid point cM | 118.45 | | G-T | G-G | A-T | A-G |
| | P value | 0.012 | Freq | 0.06 | 0.11 | 0.38 | 0.45 |
| | | | Effect | 0.302 | 0.238 | 0.034 | 0 |
| | | | SE | 0.149 | 0.114 | 0.069 | |
| | | | P value | 0.043 | 0.037 | 0.619 | |

| HAP24 | Haplotype Overall | | | Individual Haplotypes | | | |
|---|---|---|---|---|---|---|---|
| FCR | mid point cM | 118.45 | | G-T | G-G | A-T | A-G |
| | P value | 0.070 | Freq | 0.06 | 0.11 | 0.38 | 0.45 |
| | | | Effect | 0.389 | 0.230 | 0.053 | 0 |
| | | | SE | 0.196 | 0.160 | 0.091 | |
| | | | P value | 0.048 | 0.150 | 0.558 | |

| HAP24 | Haplotype Overall | | | Individual Haplotypes | | | |
|---|---|---|---|---|---|---|---|
| PEG | mid point cM | 118.45 | | C-A | C-C | T-A | T-C |
| | P value | 0.041 | Freq | 0.06 | 0.11 | 0.38 | 0.45 |
| | | | Effect | −0.019 | −0.008 | 0.0005 | 0 |
| | | | SE | 0.008 | 0.006 | 0.004 | |
| | | | P value | 0.024 | 0.235 | 0.903 | |

TABLE 3

BTA5 SNP allele substitution effects and ls means.

| SNP36-pRFI | | | | Genotype | | |
|---|---|---|---|---|---|---|
| cM | 91.6 | | | T/T | T/C | C/C |
| Allele Sub. Effect | −0.172 | Freq | | 0.092 | 0.469 | 0.439 |
| SE | 0.062 | LS Mean | | 0.296 | 0.011 | −0.110 |
| pvalue | 0.005 | SE | | 0.130 | 0.070 | 0.070 |

| SNP36-gRFI | | | | Genotype | | |
|---|---|---|---|---|---|---|
| cM | 91.6 | | | T/T | T/C | C/C |
| Allele Sub. Effect | −0.167 | Freq | | 0.092 | 0.469 | 0.439 |
| SE | 0.064 | LS Mean | | 0.143 | −0.132 | −0.249 |
| pvalue | 0.009 | SE | | 0.132 | 0.068 | 0.068 |

| SNP36-DMI | | | | Genotype | | |
|---|---|---|---|---|---|---|
| cM | 91.6 | | | T/T | T/C | C/C |
| Allele Sub. Effect | −0.222 | Freq | | 0.092 | 0.469 | 0.439 |
| SE | 0.091 | LS Mean | | 10.81 | 10.58 | 10.36 |
| pvalue | 0.015 | SE | | 0.21 | 0.13 | 0.14 |

| SNP36-PEG | | | | Genotype | | |
|---|---|---|---|---|---|---|
| cM | 91.6 | | | T/T | T/C | C/C |
| Allele Sub. Effect | 0.008 | Freq | | 0.092 | 0.469 | 0.439 |
| SE | 0.004 | LS Mean | | 0.273 | 0.288 | 0.292 |
| pvalue | 0.035 | SE | | 0.007 | 0.004 | 0.004 |

TABLE 4

BTA 5 Haplotype effects and associations.

| HAP34 | Haplotype Overall | | | | Individual Haplotypes | | |
|---|---|---|---|---|---|---|---|
| pRFI | mid point cM | 91.45 | | | G-C | A-C | G-T |
| | P value | 0.045 | Freq | | 0.581 | 0.092 | 0.326 |
| | | | Effect | | −0.170 | −0.185 | 0 |
| | | | SE | | 0.066 | 0.128 | |
| | | | P value | | 0.011 | 0.150 | |
| HAP34 | Haplotype Overall | | | | Individual Haplotypes | | |
| gRFI | mid point cM | 91.45 | | | G-C | A-C | G-T |
| | P value | 0.069 | Freq | | 0.581 | 0.092 | 0.326 |
| | | | Effect | | −0.163 | −0.199 | 0 |
| | | | SE | | 0.069 | 0.133 | |
| | | | P value | | 0.018 | 0.135 | |
| HAP34 | Haplotype Overall | | | | Individual Haplotypes | | |
| DMI | mid point cM | 91.45 | | | G-C | A-C | G-T |
| | P value | 0.044 | Freq | | 0.581 | 0.092 | 0.326 |
| | | | Effect | | −0.221 | −0.187 | 0 |
| | | | SE | | 0.098 | 0.188 | |
| | | | P value | | 0.025 | 0.320 | |
| HAP35 | Haplotype Overall | | | | Individual Haplotypes | | | |
| pRFI | mid point cM | 91.7 | | | C-A | T-G | T-A | C-G |
| | P value | 0.016 | Freq | | 0.557 | 0.027 | 0.300 | 0.117 |
| | | | Effect | | 0.146 | 0.523 | 0.275 | 0 |
| | | | SE | | 0.100 | 0.277 | 0.099 | |
| | | | P value | | 0.147 | 0.059 | 0.006 | |
| HAP35 | Haplotype Overall | | | | Individual Haplotypes | | | |
| gRFI | mid point cM | 91.7 | | | C-A | T-G | T-A | C-G |
| | P value | 0.011 | Freq | | 0.557 | 0.027 | 0.300 | 0.117 |
| | | | Effect | | 0.191 | 0.585 | 0.303 | 0 |
| | | | SE | | 0.098 | 0.283 | 0.099 | |
| | | | P value | | 0.053 | 0.039 | 0.002 | |
| HAP35 | Haplotype Overall | | | | Individual Haplotypes | | | |
| PEG | mid point cM | 91.7 | | | C-A | T-G | T-A | C-G |
| | P value | 0.051 | Freq | | 0.557 | 0.027 | 0.300 | 0.117 |
| | | | Effect | | −0.009 | −0.029 | −0.014 | 0 |
| | | | SE | | 0.006 | 0.016 | 0.006 | |
| | | | P value | | 0.097 | 0.074 | 0.011 | |

TABLE 5

BTA 10 Haplotype associations and effects.

| HAP30 | Overall Haplotype | | | | Individual Haplotypes | | | |
|---|---|---|---|---|---|---|---|---|
| pRFI | Mid point cM | 114.5 | | | C-T | G-T | G-A | C-A |
| | P value | 0.001 | Freq | | 0.367 | 0.557 | 0.020 | 0.057 |
| | | | Effect | | 0.512 | 0.332 | 0.611 | 0 |
| | | | SE | | 0.136 | 0.128 | 0.279 | |
| | | | P value | | 0.000 | 0.010 | 0.029 | |
| HAP30 | Overall Haplotype | | | | Individual Haplotypes | | | |
| gRFI | Mid point cM | 114.5 | | | C-T | G-T | G-A | C-A |
| | P value | 0.001 | Freq | | 0.367 | 0.557 | 0.020 | 0.057 |
| | | | Effect | | 0.548 | 0.353 | 0.696 | 0 |
| | | | SE | | 0.140 | 0.131 | 0.287 | |
| | | | P value | | 0.0001 | 0.007 | 0.016 | |

TABLE 5-continued

BTA 10 Haplotype associations and effects.

| HAP30 | Overall Haplotype | | | Individual Haplotypes | | | |
|---|---|---|---|---|---|---|---|
| DMI | Mid point cM | 114.5 | | C-T | G-T | G-A | C-A |
| | P value | 0.054 | Freq | 0.367 | 0.557 | 0.020 | 0.057 |
| | | | Effect | 0.500 | 0.368 | 0.175 | 0 |
| | | | SE | 0.204 | 0.193 | 0.412 | |
| | | | P value | 0.015 | 0.058 | 0.671 | |

| HAP30 | Overall Haplotype | | | Individual Haplotypes | | | |
|---|---|---|---|---|---|---|---|
| FCR | Mid point cM | 114.5 | | C-T | G-T | G-A | C-A |
| | P value | 0.013 | Freq | 0.367 | 0.557 | 0.020 | 0.057 |
| | | | Effect | 0.580 | 0.404 | 0.669 | 0 |
| | | | SE | 0.184 | 0.175 | 0.374 | |
| | | | P value | 0.002 | 0.021 | 0.074 | |

| HAP30 | Overall Haplotype | | | Individual Haplotypes | | | HAP30 |
|---|---|---|---|---|---|---|---|
| PEG | Mid point cM | 114.5 | | C-T | G-T | G-A | C-A |
| | P value | | Freq | 0.367 | 0.557 | 0.020 | 0.057 |
| | | | Effect | −0.032 | −0.022 | −0.038 | 0 |
| | | | SE | 0.008 | 0.007 | 0.016 | |
| | | | P value | 7.94E−05 | 0.003 | 0.019 | |

TABLE 6

BTA20 SNP allele substitution effects and ls means.

| SNP50-pRFI | | | | Genotype | | |
|---|---|---|---|---|---|---|
| cM | 42.7 | | | A/A | A/G | G/G |
| Allele Sub. Effect | 0.159 | Freq | | 0.079 | 0.423 | 0.498 |
| SE | 0.064 | LSmean | | −0.386 | −0.036 | 0.059 |
| pvalue | 0.013 | SE | | 0.145 | 0.065 | 0.062 |

| SNP50-gRFI | | | | Genotype | | |
|---|---|---|---|---|---|---|
| cM | 42.7 | | | A/A | A/G | G/G |
| Allele Sub. Effect | 0.181 | Freq | | 0.079 | 0.423 | 0.498 |
| SE | 0.063 | LSmean | | −0.594 | −0.181 | −0.081 |
| pvalue | 0.004 | SE | | 0.144 | 0.061 | 0.057 |

| SNP50-DMI | | | | Genotype | | |
|---|---|---|---|---|---|---|
| cM | 42.7 | | | A/A | A/G | G/G |
| Allele Sub. Effect | 0.200 | Freq | | 0.079 | 0.423 | 0.498 |
| SE | 0.098 | LSmean | | 10.205 | 10.444 | 10.632 |
| pvalue | 0.041 | SE | | 0.241 | 0.137 | 0.136 |

| SNP50-FCR | | | | Genotype | | |
|---|---|---|---|---|---|---|
| cM | 42.7 | | | A/A | A/G | G/G |
| Allele Sub. Effect | 0.198 | Freq | | 0.079 | 0.423 | 0.498 |
| SE | 0.088 | LSmean | | 6.846 | 7.253 | 7.382 |
| pvalue | 0.026 | SE | | 0.205 | 0.103 | 0.101 |

| SNP50-PEG | | | | Genotype | | |
|---|---|---|---|---|---|---|
| cM | 42.7 | | | A/A | A/G | G/G |
| Allele Sub. Effect | −0.011 | Freq | | 0.079 | 0.423 | 0.498 |
| SE | 0.004 | LSmean | | 0.315 | 0.289 | 0.284 |
| pvalue | 0.003 | SE | | 0.008 | 0.004 | 0.003 |

TABLE 7

BTA 20 Haplotype efects and associations

| HAP18 | Haplotype Overall | | | Individual Haplotypes | | | |
|---|---|---|---|---|---|---|---|
| pRFI | Mid point cM | 42.7 | | G-G | A-G | A-A | G-A |
| | P value | 0.093 | Freq | 0.490 | 0.219 | 0.062 | 0.229 |
| | | | Effect | 0.139 | 0.150 | −0.079 | 0 |
| | | | SE | 0.082 | 0.086 | 0.163 | |
| | | | P value | 0.091 | 0.084 | 0.630 | |

| HAP18 | Haplotype Overall | | | Individual Haplotypes | | | |
|---|---|---|---|---|---|---|---|
| gRFI | Mid point cM | 42.7 | | G-G | A-G | A-A | G-A |
| | P value | 0.035 | Freq | 0.490 | 0.219 | 0.062 | 0.229 |
| | | | Effect | 0.166 | 0.166 | −0.076 | 0 |
| | | | SE | 0.082 | 0.085 | 0.165 | |
| | | | P value | 0.043 | 0.050 | 0.647 | |

TABLE 7-continued

BTA 20 Haplotype efects and associations

| HAP18 | Haplotype Overall | | | Individual Haplotypes | | | |
|---|---|---|---|---|---|---|---|
| PEG | Mid point cM | 42.7 | | G-G | A-G | A-A | G-A |
| | P value | 0.023 | Freq | 0.490 | 0.219 | 0.062 | 0.229 |
| | | | Effect | −0.008 | −0.011 | 0.008 | 0 |
| | | | SE | 0.005 | 0.005 | 0.009 | |
| | | | P value | 0.085 | 0.029 | 0.407 | |

TABLE 8

BTA29 SNP allele substitution effects and ls means.

| SNP18-pRFI | | | | Genotype | | |
|---|---|---|---|---|---|---|
| cM | 57.4 | | | AA | AG | GG |
| Allele Sub. Effect | 0.230 | Freq | | 0.050 | 0.368 | 0.582 |
| SE | 0.072 | LS Mean | | −0.235 | −0.149 | 0.122 |
| pvalue | 0.002 | SE | | 0.182 | 0.084 | 0.076 |
| SNP18-gRFI | | | | Genotype | | |
| cM | 57.4 | | | AA | AG | GG |
| Allele Sub. Effect | 0.242 | Freq | | 0.050 | 0.368 | 0.582 |
| SE | 0.074 | LS Mean | | −0.370 | −0.309 | −0.015 |
| pvalue | 0.001 | SE | | 0.187 | 0.084 | 0.075 |
| SNP18-PEG | | | | Genotype | | |
| cM | 57.4 | | | AA | AG | GG |
| Allele Sub. Effect | −0.009 | Freq | | 0.050 | 0.368 | 0.582 |
| SE | 0.004 | LS Mean | | 0.294 | 0.294 | 0.283 |
| pvalue | 0.039 | SE | | 0.010 | 0.004 | 0.004 |

TABLE 9

BTA 29 Haplotype associations and effects.

| HAP28 | Haplotype Overall | | | Individual Haplotypes | | | |
|---|---|---|---|---|---|---|---|
| pRFI | Mid point cM | 57.6 | | T-G | C-G | C-A | T-A |
| | pvalue | 0.002 | Freq | 0.758 | 0.070 | 0.003 | 0.169 |
| | | | Effect | 0.195 | 0.146 | 2.537 | 0 |
| | | | SE | 0.077 | 0.129 | 0.758 | |
| | | | P value | 0.012 | 0.257 | 0.001 | |

| HAP28 | Haplotype Overall | | | Individual Haplotypes | | | |
|---|---|---|---|---|---|---|---|
| gRFI | Mid point cM | 57.6 | | T-G | C-G | C-A | T-A |
| | pvalue | 0.002 | Freq | 0.758 | 0.070 | 0.003 | 0.169 |
| | | | Effect | 0.177 | 0.110 | 2.627 | 0 |
| | | | SE | 0.074 | 0.129 | 0.774 | |
| | | | P value | 0.017 | 0.396 | 0.001 | |

| HAP28 | Haplotype Overall | | | Individual Haplotypes | | | |
|---|---|---|---|---|---|---|---|
| DMI | Mid point cM | 57.6 | | T-G | C-G | C-A | T-A |
| | pvalue | 0.012 | Freq | 0.758 | 0.070 | 0.003 | 0.169 |
| | | | Effect | 0.304 | 0.369 | 2.433 | 0 |
| | | | SE | 0.118 | 0.193 | 1.130 | |
| | | | P value | 0.010 | 0.057 | 0.032 | |

| HAP28 | Haplotype Overall | | | Individual Haplotypes | | | |
|---|---|---|---|---|---|---|---|
| PEG | Mid point cM | 57.6 | | T-G | C-G | C-A | T-A |
| | pvalue | 0.095 | Freq | 0.758 | 0.070 | 0.003 | 0.169 |
| | | | Effect | −0.008 | −0.002 | −0.090 | 0 |
| | | | SE | 0.004 | 0.007 | 0.044 | |
| | | | P value | −0.008 | −0.002 | −0.090 | 0 |

TABLE 10

Genotype frequencies of SNPs reported in the validation

| Marker | Chromosome | Genotype | Counts | Frequency | |
|---|---|---|---|---|---|
| | | | | | Reference** |
| UCP2 | 15 | CC | 14 | 0.054 | Sherman et al., 2006 |
| | | CG | 77 | 0.296 | |
| | | GG | 169 | 0.650 | |
| T945M | 3 | CC | 216 | 0.831 | Liefers et al., 2004. |
| | | CT | 39 | 0.150 | |
| | | TT | 5 | 0.019 | |
| GHR2 | 20 | AA | 192 | 0.738 | Sherman et al., 2006 |
| | | AG | 61 | 0.235 | |
| | | GG | 7 | 0.027 | |
| FGF8SNP15 | 26 | CC | 30 | 12.05 | Marques et al., 2007 |
| | | CT | 111 | 44.58 | |
| | | TT | 108 | 43.37 | |
| DECRSNP5 | 14 | CC | 4 | 0.015 | Marques et al., 2006 |
| | | CT | 67 | 0.258 | |
| | | TT | 189 | 0.727 | |
| CBFA2TSNP2 | 14 | AA | 12 | 0.046 | Marques et al., 2006 |
| | | AC | 66 | 0.254 | |
| | | CC | 179 | 0.688 | |
| BTA5SNP35 | 5 | AA | 1 | 0.004 | Sherman et al., 2007 |
| | | AG | 22 | 0.085 | |
| | | GG | 231 | 0.888 | |
| BTA2SNP24 | 2 | AA | 122 | 0.477 | Sherman et al., 2007 |
| | | AC | 115 | 0.449 | |
| | | CC | 19 | 0.074 | |
| BTA2SNP25 | 2 | AA | 146 | 0.570 | Sherman et al., 2007 |
| | | AG | 95 | 0.371 | |
| | | GG | 15 | 0.059 | |
| | | | | | Reference[a]** |
| BTA2SNP26 | 2 | GG | 99 | 0.381 | Sherman et al., 2007 |
| | | GT | 124 | 0.477 | |
| | | TT | 37 | 0.142 | |
| BTA29SNP18 | 29 | AA | 13 | 0.051 | Sherman et al., 2007 |
| | | AG | 71 | 0.281 | |
| | | GG | 169 | 0.668 | |
| BTA10SNP32 | 10 | AT | 16 | 0.062 | Sherman et al., 2007 |
| | | TT | 244 | 0.938 | |
| BETALAC | 11 | CC | 149 | 0.575 | Kuss et al., 2003 |
| | | CT | 96 | 0.371 | |
| | | TT | 14 | 0.054 | |
| A59V | 4 | CC | 217 | 0.838 | Nkrumah et al., 2006 |
| | | CT | 39 | 0.151 | |
| | | TT | 3 | 0.012 | |
| A252T | 4 | AA | 229 | 0.881 | Lagonigro et al., 2002 |
| | | AT | 30 | 0.115 | |
| | | TT | 1 | 0.004 | |

[a]Some markers may have been previously reported in the literature for traits measured in dairy cattle instead of beef cattle.
**Cited References are:
1. Archer, J. A., E. C. Richardson, R. M. Herd, and P. F. Arthur. 1999. Potential for selection to improve efficiency of feed use in beef cattle: a review. Aust. J. Agric. Res. 50: 147-161.
2. Arthur, P. F., J. A. Archer, D. J. Johnson, R. M. Herd, E. C. Richardson, and P. F. Parnell. 2001. Genetic and phenotypic variance and covariance components for feed intake, feed efficiency and other postweaning traits in Angus cattle. J. Anim. Sci. 79: 2805-2811.
3. Basarab, J.., M. A. Price, J. L. Aalhus, E. K. Okine, W. M. Snelling, and K. L. Lyle. 2003. Residual feed intake and body composition in young growing cattle. Can. J. Anim. Sci. 83: 189-204.
4. Basarab, J. A., Ramsey, P., Crews, D., Lyle, K. L., Moore, S. S. and Okine, E. K. 2005. Commercialization of net feed efficiency in beef cattle: Trait variance and economic potential. In: Commercialization of net feed efficiency in beef cattle. Alberta Agriculture Research Institute, Project Number: 2002A090R. Alberta Agriculture, Food and Rural Development, Lacombe Research Centre, 6000 C & E Trail, Lacombe, AB, T4L 1W1, Final Report, p. 10-38.
5. Basarab, J. A., D. McCartney, E. K. Okine, and V. S. Baron. 2007. Relationships between progeny residual feed intake and dam productivity traits. Can. J. Anim. Sci. (In Press).
6. Brethour, J. R. 1992. The repeatability and accuracy of ultrasound in measuring backfat in cattle. J. Anim. Sci. 70: 1039-1044.
7. Carstens, G. and Tedeschi, L. 2006. Feed efficiency traits for growing cattle. National Beef Cattle Evaluation Consortium, Feed Efficiency Symposium, Dec. 14-15, 2006, Kansas City, MO, USA.
8. CCAC Canadian Council on Animal Care 1993. Guide to the care and use of experimental animals. In: Olfert, E. D., Cross, B. M., McWilliams, A. A. (Eds.), Canadian Council on Animal Care, vol. 1. Ottawa ON.
9. Crews, D. H., Jr., Pollak, E. J., Weaber, R. L., Quaas, R. L. and Lipsey, R. J. 2003. Genetic parameters for carcass traits and their live animal indicators in Simmental cattle. J. Anim. Sci. 81: 1427-1433.
10. Crews, D. H. Jr., 2005. Genetics of efficient feed utilization and national cattle
11. evaluation: a review. Genet. Mol. Res. 4: 152-165. (reference not cited in text)
12. Crews Jr., D. H., Carstens, G. E. and Lancaster, P. A. 2005. Development of a multiple trait selection index for feedlot traits in beef cattle including feed efficiency. Proc. West. Sec. Am. Soc. Anim. Sci. 56: 71-74.
13. Falconer, D. S., and T. F. C. Mackay. 1996. Introduction to Quantitative Genetics. Harlow, Esse: Addison Wesley Longman. 464pp.
14. Gilmour, A. R., B. R. Cullis, S. J. Welham, and R. Thompson. 2000. ASREML reference manual. IACR-Rothamsted Experimental Station, Harpenden, UK.
15. Herd, R. M., J. A. Archer and P. F. Arthur. 2003. Reducing the cost of beef production through genetic improvement feed intake: Opportunity and challenges to application. J. Anim. Sci. 81(E. Suppl. 1): E9-E17.

TABLE 10-continued

Genotype frequencies of SNPs reported in the validation

| Marker | Chromosome | Genotype | Counts | Frequency |
|---|---|---|---|---|

16. Johnson, D. E., C. L. Ferrell, and T. G. Jenkins. 2003. The history of energetic efficiency research: Where have we been and where are we going? J. Anim. Sci. 2003. 81: E27-E38.
17. Kuss, A. W. J. Gogol and H. Geldermann. 2003. Associations of a Polymorphic AP-2 Binding Site in the 5'-Flanking Region of the Bovine β-Lactoglobulin Gene with Milk Proteins. J. Dairy Sci. 86: 2213-2218.
18. Lagonigro, R., Wiener, P., Pilla, F., Woolliams, J. A. and Williams, J. L. 2003. A new mutation in the coding region of the bovine leptin gene associated with feed intake. Animal Genetics 34: 371-374.
19. Liefers, S. C., R. F. Veerkamp, M. F. W. te Pas, C. Delavaud, Y. Chilliard, T. van der Lende. 2004. A missense mutation in the bovine leptin receptor gene is associated with leptin concentrations during late pregnancy. Animal Genetics 35: 138-141.
20. Marques, E. F., J. D. Nkrumah, S. S. Moore. 2006. Polymorphisms in two positional candidate genes in the bovine chromosome 14 are associated with carcass merit in beef cattle. 2006. Plant & Animal Genomes XIV Conference, Town & Country Convention Center San Diego, CA. P523.
21. Marques, E. F., J. D. Nkrumah, S. S. Moore. 2007. Polymorphisms in the bovine fibroblastgrowth factor 8 (fgf8) gene are associated with carcass quality and growth traits in beef cattle. 2007. Town & Country Convention Center, San Diego, CA. W69.
22. Moore, S. S., D. H. Crews, Jr, and J. D. Nkrumah. 2006a. Multiple and candidate gene approaches to genetic evaluation of feed efficiency in beef cattle. Proc. 8th World Congr. Genet. Appl. Livest. Prod. 14-01, August 13-18, Belo Horizonte, MG, Brasil.
23. Moore, SS., J. D. Nkrumah, C. Li, R. Bartusiak, E. L. Sherman, B. Murdoch, S. D. McKay, and Z. Wang. 2006b. Genome-wide scan for QTL affecting feed intake and feed efficiency in beef cattle. Plant & Animal Genomes XIV Conference, Town & Country Convention Center San Diego, CA. P520.
24. Nkrumah, J. D., C. Li, Z. Wang, R. Bartusiak, B. Murdoch, J. Basarab, D. Crews, and S. S. Moore. 2005. Full genome scan for quantitative trait loci (QTL) for net feed efficiency in beef cattle. J. Anim. Sci. 83 (Suppl. 1): 13. Abstr.
25. Nkrumah, J. D., J. A. Basarab, Z. Wang, C. Li, M. A. Price, E. K. Okine, D. H. Crews, and S. S. Moore. 2007. Genetic and phenotypic relationships of feed intake and different measures of feed efficiency with growth and carcass merit of beef cattle J. Anim Sci. doi: 10.2527/jas.2006-767.
26. Nkrumah, J. D., E. K. Okine, G. W. Mathison, K. Schmid, C. Li, J. A. Basarab, M. A. Price, Z. Wang, and S. S. Moore. 2006. Relationships of feedlot feed efficiency, performance, and feeding behaviour with metabolic rate, methane production, and energy partitioning in beef cattle. J. Anim. Sci. 84: 145-153.
27. Schenkel, F. S., S. P. Miller, and J. W. Wilton. 2004. Genetic parameters and breed differences for feed efficiency, growth, and body composition traits of young beef bulls. Can. J. Anim. Sci. 84: 177-185.
28. Sherman, E. L., J. D. Nkrumah, B. M. Murdoch, C. Li, S. D. McKay, Z. Wang, and S. S. Moore. 2006. Polymorphisms in the GHR, NPY, Ghrelin, And UCP2 genes and their associations with measures of performance and carcass merit in beef cattle. Plant & Animal Genomes XIV Conference, Town & Country Convention Center San Diego, CA. P28.
29. Sherman, E. L., J. D. Nkrumah, S. S. Moore. 2007. Fine mapping and identification of polymorphisms influencing feed intake and efficiency in beef cattle. Animal Genetics (Submitted).
30. Tempelman, R. J. and G. J. M. Rosa. 2004. Empirical Bayes approaches to mixed model inference in quantitative genetics. In: Genetic analyses of complex traits Using SAS, Arnold M. Saxton, Ed., SAS Publishing, Cary, NC.

TABLE 11

Descriptive statistics and heritability estimates for the traits in the validation

| Trait | Abbrev. | N | Mean | SD | Heritability |
|---|---|---|---|---|---|
| Birth Weight, kg | BWT | 262 | 44.07 | 8.20 | 0.31 |
| Average daily gain, kg/d | ADG | 260 | 1.45 | 0.33 | 0.36 |
| Metabolic mid-test BW, $kg^{0.75}$ | MWT | 260 | 96.88 | 12.07 | 0.38 |
| Daily dry matter intake, kg/d | DMI | 260 | 9.22 | 1.29 | 0.45 |
| Feed to gain ratio, kg DM/kg gain | FCR | 260 | 6.66 | 1.66 | 0.45 |
| RFI, kg DM/d | RFIa | 260 | 0.00 | 0.59 | 0.36 |
| $RFI_{fat}$, kg DM/d | RFIb | 260 | 0.00 | 0.58 | 0.35 |
| Final ultrasound backfat, mm | BFAT | 257 | 7.55 | 2.72 | 0.41 |
| Final ultrasound marbling[c] | MBS | 260 | 4.99 | 0.63 | 0.34 |
| Final ultrasound rib eye area, $cm^2$ | REA | 257 | 73.36 | 11.69 | 0.42 |
| Lean meat yield, % | LMY | 257 | 60.27 | 2.72 | 0.43 |
| Final weight, kg | FWT | 260 | 515.61 | 82.93 | 0.47 |

[a,b]RFI is adjusted for ADG and MWT whilst $RFI_{fat}$ is adjusted for ADG, MWT, and gain in ultrasound backfat.

[c]Ultrasound marbling score is a measure of intramuscular fat: trace marbling or less = 1.00 to 3.99 (Canada A quality grade); slight marbling = 4.00 to 4.99 (Canada AA quality grade); small to moderate marbling = 5.00 to 7.99 (Canada AAA quality grade); slightly abundant or more marbling = 8.00 to 11.00 (Canada Prime).

TABLE 12

Phenotypic correlation among different measures of feed efficiency and component traits in beef cattle.

| Traits[a] | $RFI_{fat}$ | FCR | DMI | ADG | MWT |
|---|---|---|---|---|---|
| RFI | 0.966 | 0.295 | 0.460 | $0.000^{ns}$ | $0.000^{ns}$ |
| $RFI_{fat}$ | | 0.294 | 0.445 | $0.000^{ns}$ | $0.000^{ns}$ |
| FCR | | | −0.201** | −0.793 | −0.078 |
| DMI | | | | 0.700 | 0.748 |
| ADG | | | | | 0.435 |

[a]Meanings of abbreviations are listed in Table 2 above.
[ns]Not significantly different from zero;
**Significantly different from zero at $P < 0.01$.
All other correlation coefficients ate different from zero at $P < 0.001$.

TABLE 13

Phenotypic correlations of feed intake and efficiency with birth weight, final weight and ultrasound measures of carcass merit.

| Traits[a] | BWT | FWT | BFAT | MBS | REA | LMY |
|---|---|---|---|---|---|---|
| RFI | −0.143* | −0.004 | 0.219** | 0.248** | −0.031 | −0.242* |
| $RFI_{fat}$ | −0.114* | −0.003 | 0.120* | 0.145* | −0.024 | −0.013 |
| FCR | 0.073† | −0.266** | −0.234** | −0.137* | −0.205** | 0.129* |
| DMI | 0.340** | 0.834*** | 0.396*** | 0.104* | 0.566*** | −0.099† |

[a]Meanings of abbreviations are listed in Table 2 above.
†Tendentiously different from zero at $P < 0.01$;
*Significantly different from zero at $P < 0.05$;
**Significantly different from zero at $P < 0.01$;
***Significantly different from zero at $P < 0.001$;
All other correlation coefficients ate different from zero at $P < 0.001$.

TABLE 14

Association of individual single markers
with feed intake and feed efficiency in the validation

| Trait[a] | Marker | Allele Substitution[b] α | P-value | Fixed Effect[b] ProbF | Additive Effect a | P-value | Dominance Deviation d | P-value |
|---|---|---|---|---|---|---|---|---|
| DMI | DECRSNP5 | −0.447 | 0.001 | 0.004 | −0.427 | 0.096 | −0.026 | 0.927 |
| | BTA2SNP25 | 0.329 | 0.002 | 0.006 | 0.274 | 0.048 | −0.105 | 0.541 |
| | CBFA2TSNP2 | −0.377 | 0.002 | 0.005 | −0.501 | 0.002 | 0.241 | 0.221 |
| | UCP2 | −0.264 | 0.018 | 0.011 | −0.096 | 0.504 | −0.340 | 0.063 |
| | BTA5SNP35 | 0.404 | 0.060 | 0.030 | 1.285 | 0.013 | −1.049 | 0.061 |
| | BETALAC | 0.203 | 0.060 | 0.094 | 0.100 | 0.483 | −0.197 | 0.271 |
| | BTA2SNP26 | −0.187 | 0.065 | 0.023 | −0.114 | 0.282 | 0.272 | 0.043 |
| | GHR2 | −0.201 | 0.108 | 0.276 | −0.198 | 0.321 | 0.005 | 0.984 |
| FCR | DECRSNP5 | −0.376 | 0.003 | 0.010 | −0.488 | 0.045 | 0.144 | 0.589 |
| | BTA10SNP32 | 0.551 | 0.035 | 0.035 | — | — | — | — |
| | BETALAC | 0.204 | 0.045 | 0.094 | 0.279 | 0.039 | 0.143 | 0.395 |
| | CBFA2TSNP2 | −0.196 | 0.098 | 0.247 | −0.172 | 0.262 | −0.046 | 0.806 |
| | FGF8SNP15 | −0.1528 | 0.090 | 0.0934 | −0.077 | 0.102 | −0.112 | 0.421 |
| RFI | T945M | 0.259 | 0.003 | 0.013 | 0.281 | 0.040 | 0.036 | 0.833 |
| | BTA29SNP18 | −0.191 | 0.004 | 0.005 | −0.276 | 0.002 | 0.167 | 0.134 |
| | A252T | 0.286 | 0.010 | 0.008 | −0.215 | 0.476 | −0.570 | 0.075 |
| | BTA2SNP24 | −0.150 | 0.016 | 0.038 | −0.114 | 0.127 | 0.082 | 0.380 |
| | BTA5SNP35 | 0.270 | 0.033 | 0.003 | 0.997 | 0.001 | −0.867 | 0.008 |
| | A59V | 0.199 | 0.033 | 0.053 | 0.021 | 0.905 | −0.236 | 0.245 |
| RFI$_{fat}$ | BTA29SNP18 | −0.185 | 0.003 | 0.007 | −0.244 | 0.003 | 0.118 | 0.271 |
| | BTA2SNP24 | −0.153 | 0.010 | 0.031 | −0.133 | 0.060 | 0.046 | 0.607 |
| | BTA10SNP32 | 0.336 | 0.032 | 0.032 | — | — | — | — |
| | A252T | 0.218 | 0.040 | 0.041 | −0.182 | 0.529 | −0.455 | 0.138 |
| | BTA5SNP35 | 0.237 | 0.049 | 0.002 | 1.005 | 0.001 | −0.914 | 0.003 |
| | BETALAC | 0.117 | 0.055 | 0.158 | 0.125 | 0.122 | 0.015 | 0.882 |

[a]Meanings of abbreviations are listed in Table 2 above.
[b]Marker alleles were coded as 2, 1, and 0 based on the number of copies of the first alphabet of the genotypes.
[c]P-value from the fixed effects of the marker genotypes

TABLE 15

Combined effects of a panel of different markers on feed
intake and feed efficiency

| Trait[a] | Genotypic Effect[b] | P-value[c] | Variance (%)[d] |
|---|---|---|---|
| DMI | 4.900 | 7.55E−11 | 13.88 |
| FCR | 3.080 | 7.75E−05 | 5.23 |
| RFI | 1.947 | 1.34E−06 | 10.99 |
| RFI$_{fat}$ | 2.075 | 9.60E−06 | 10.15 |

[a]Meanings of abbreviations are listed in Table 2 above.
[b]Twice the allele substitution effects of the combination of markers in the panel, and is equivalent to the difference in marker effects between the best genotype combination and the worst genotype combination.
[c]SAS estimate P-value testing whether the estimated genotype effects of the combined marker panel is significantly different from zero.
[d]Proportion of the overall variance in the trait explained by the combined effects of the markers.

TABLE 16

Association of the combined panels for feed intake and
feed efficiency on growth and carcass merit

| Trait | RFI$_{fat}$ | RFI | DMI | FCR |
|---|---|---|---|---|
| BWT | 0.252 | 0.032 | 1.13E−06 | 1.97E−04 |
| ADG | 0.609 | 0.812 | 0.006 | 0.799 |
| MWT | 0.690 | 0.259 | 3.09E−10 | 1.67E−04 |
| FWT | 0.555 | 0.291 | 8.06E−10 | 0.001 |
| BFAT | 0.002 | 1.24E−06 | 0.972 | 0.845 |
| MBS | 0.394 | 0.008 | 0.973 | 0.122 |
| REA | 0.115 | 0.058 | 0.001 | 0.180 |
| LMY | 4.96E−04 | 2.79E−07 | 0.186 | 0.744 |
| RFI$_{fat}$ | — | 2.45E−05 | 0.004 | 0.073 |
| RFI | 1.52E−05 | — | 0.003 | 0.123 |
| DMI | 0.043 | 0.052 | — | 0.002 |
| FCR | 0.006 | 0.109 | 0.008 | — |

Example 2

Figure 20:
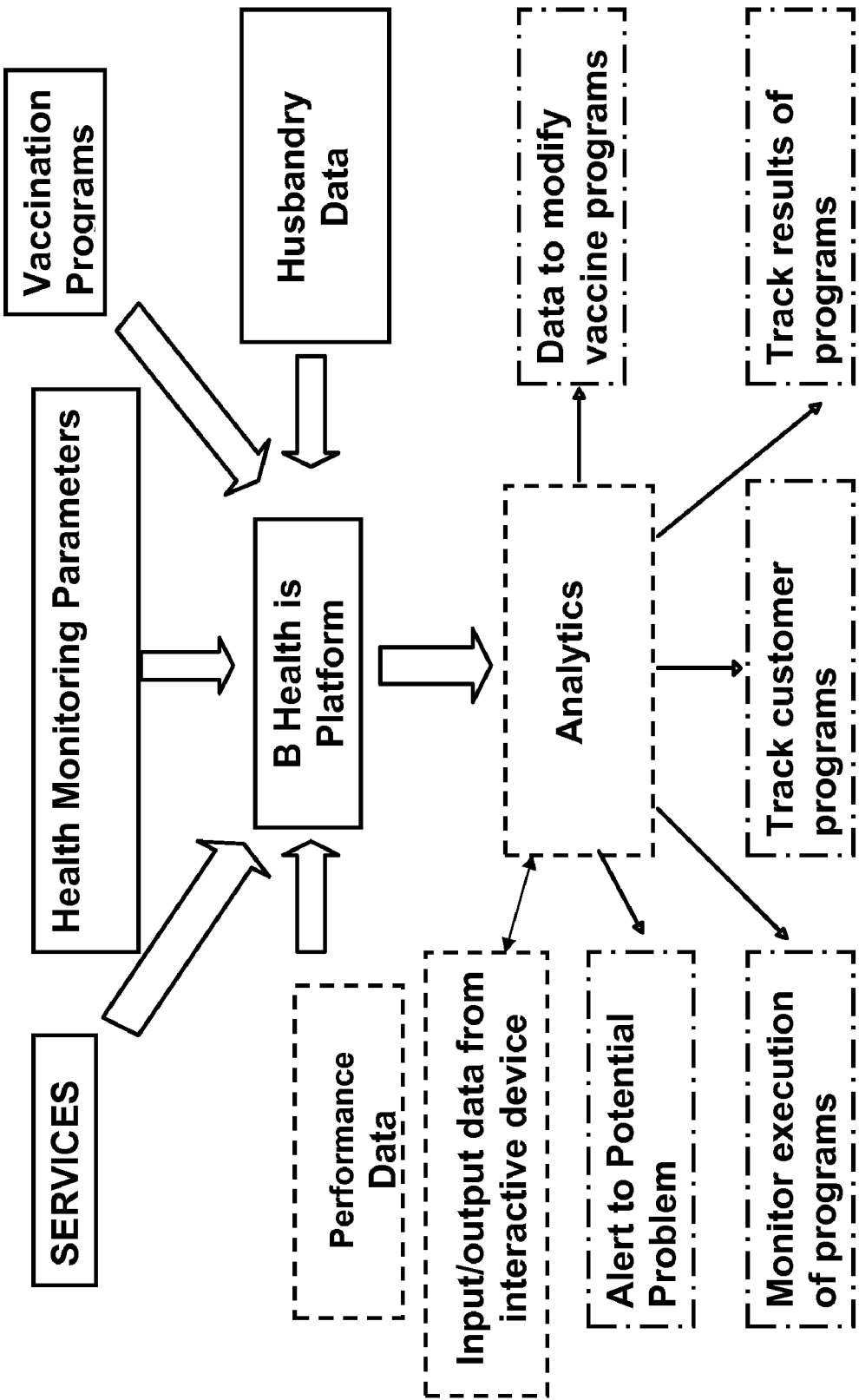
FIG. 20 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 20 shows a flowchart of the input of data and the output of results from the analysis and correlation of the data pertaining to the breeding, veterinarian histories and performance requirements of a group of animals such as from bovines. The flowchart illustrated in FIG. 20 further indicate the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 21:
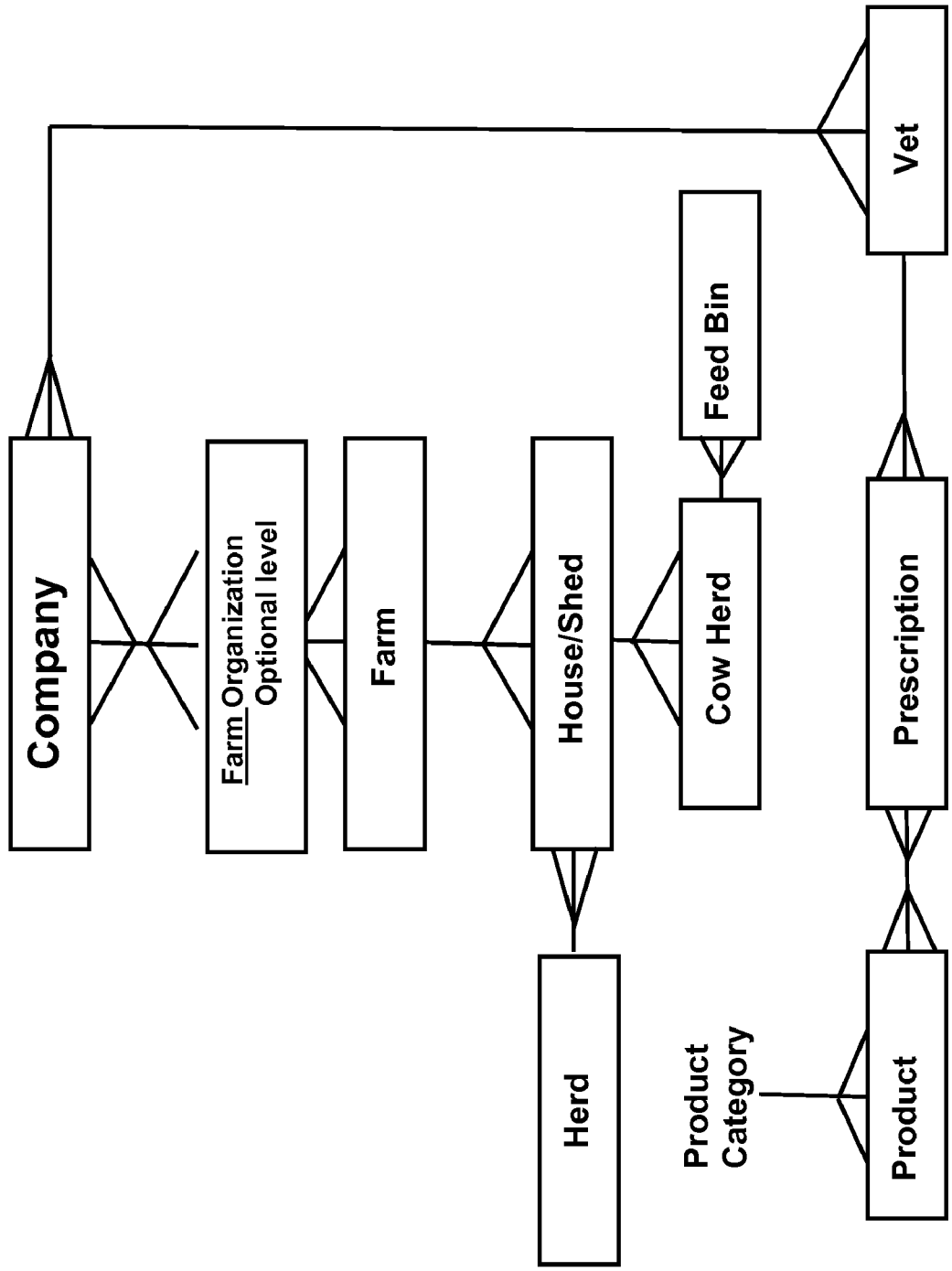
FIG. 21 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 21 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

Figure 22A:
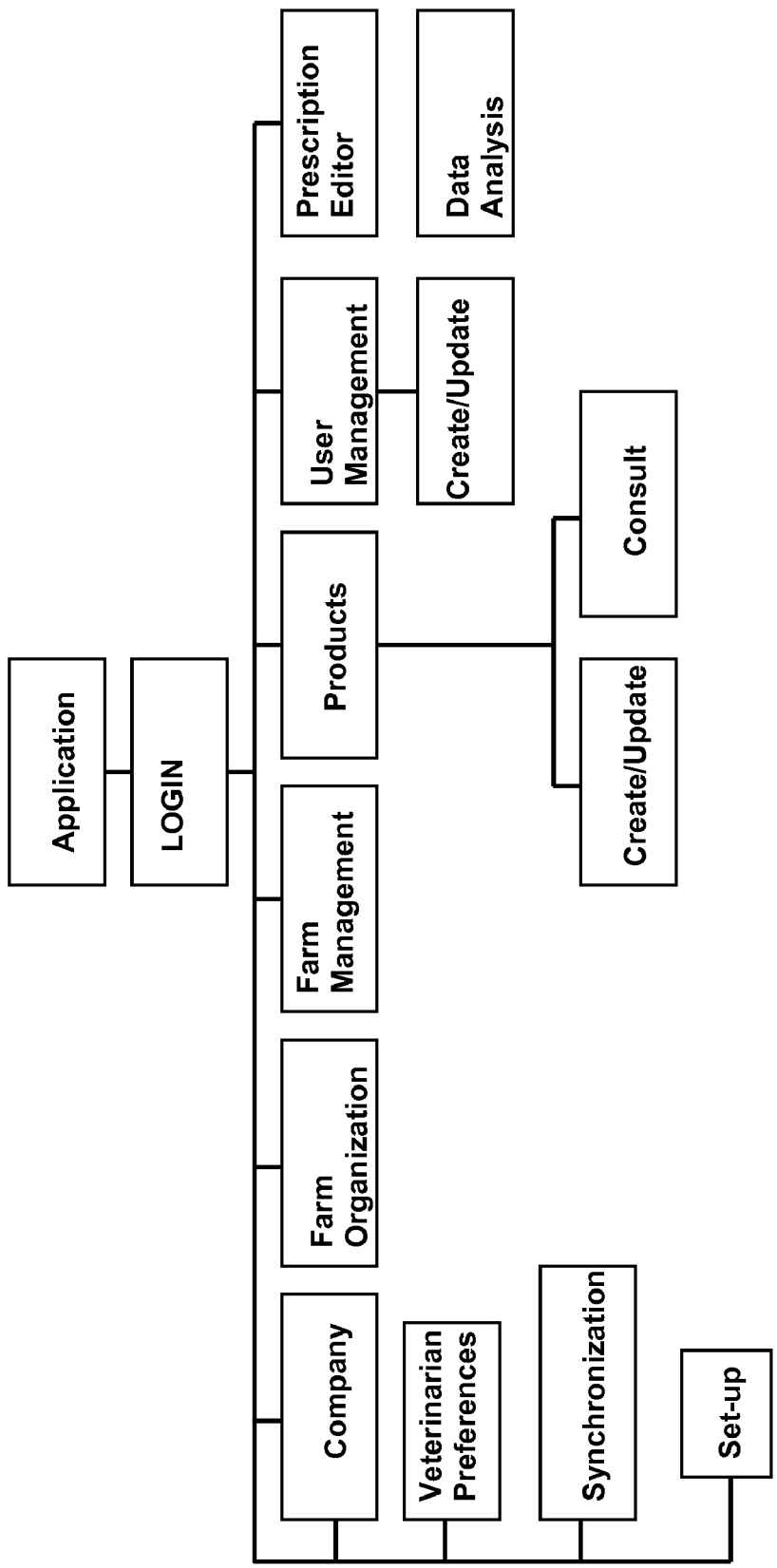
FIG. 22A illustrates the flow of events in the use of the portable computer-based system for data entry on the breeding and rearing of a herd of cows.
Figure 22B:
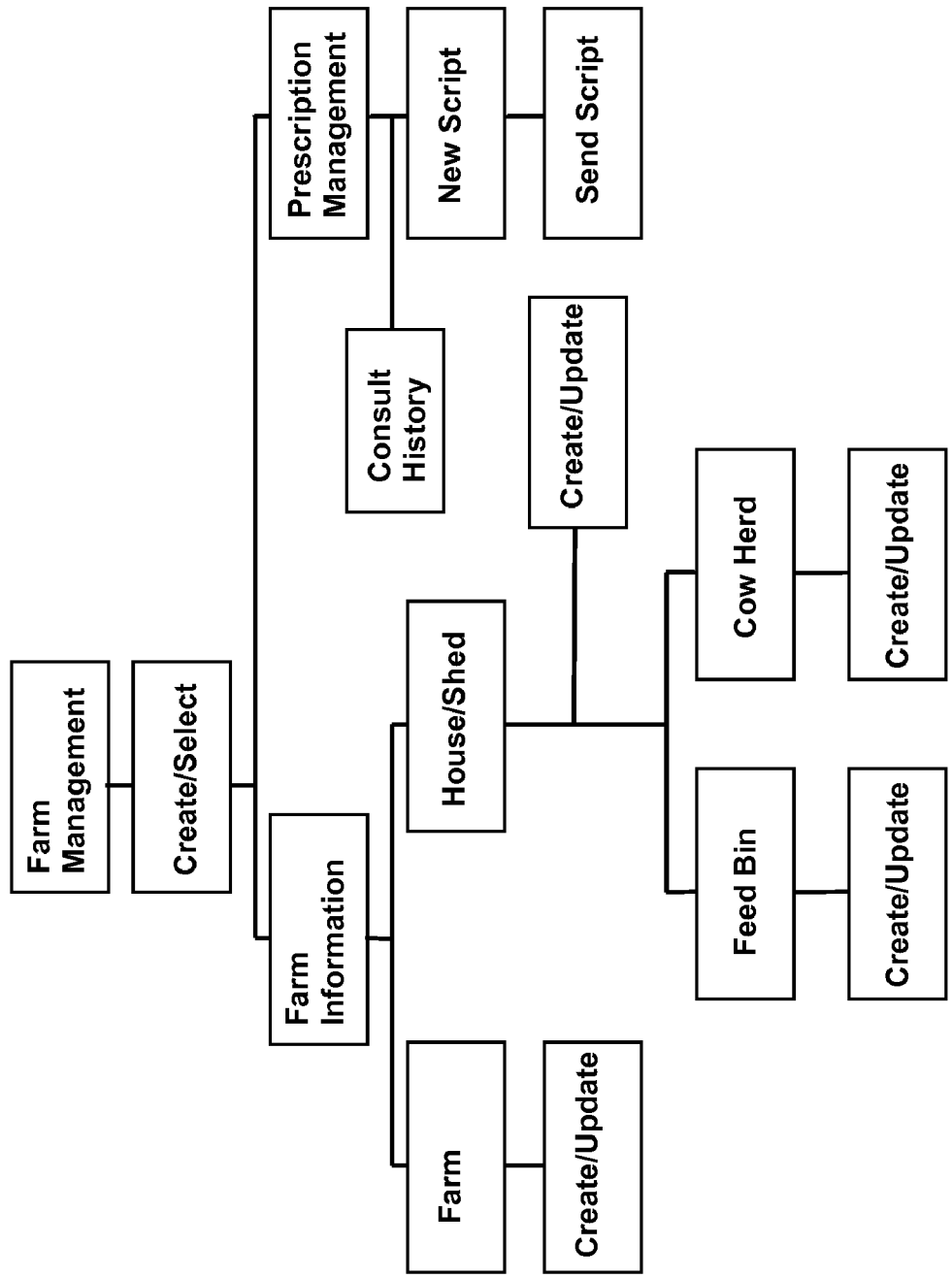
FIG. 22B illustrates the flow of events through the subroutines related to data entry concerning farm management.
Figure 22C:
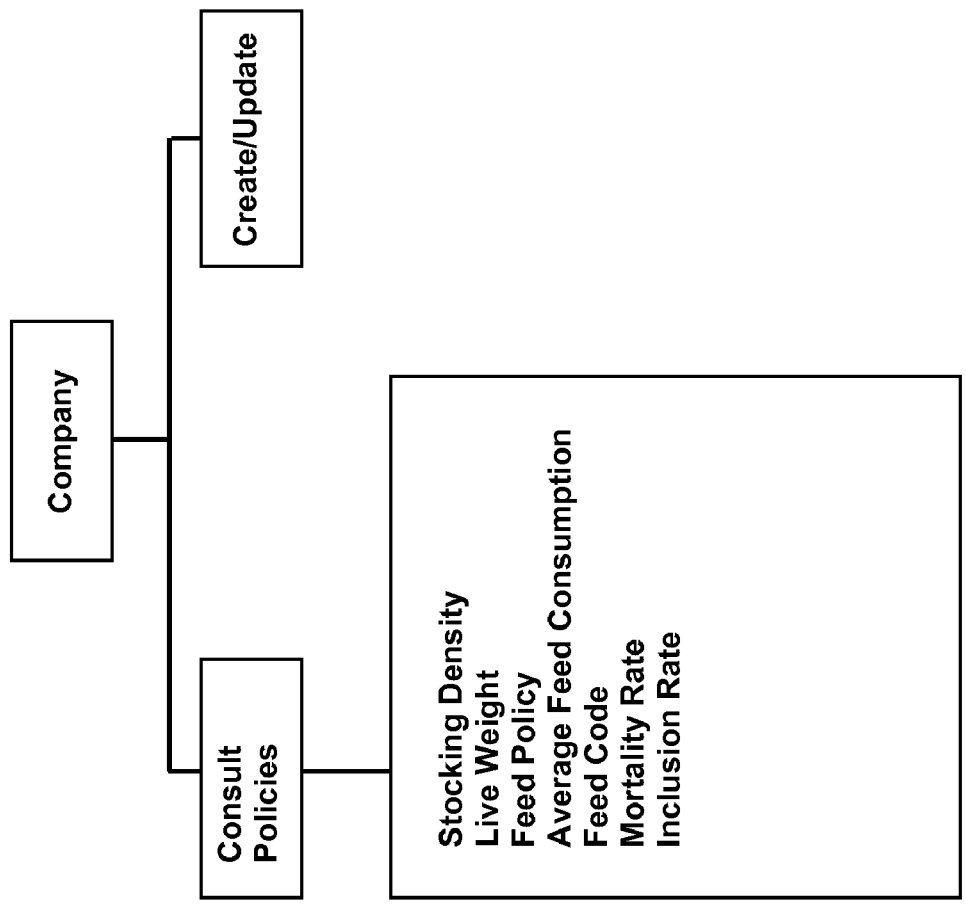
FIG. 22C illustrates the flow of events through the subroutines related to data entry concerning data specific to a company.

FIG. 22A illustrates the flow of events in the use of the portable computer-based system for data entry on the breeding and rearing of a herd of cows. FIG. 22B illustrates the flow of events through the sub-routines related to data entry concerning farm management. FIG. 22C illustrates the flow of events through the sub-routines related to data entry concerning data specific to a company.

Figure 23:
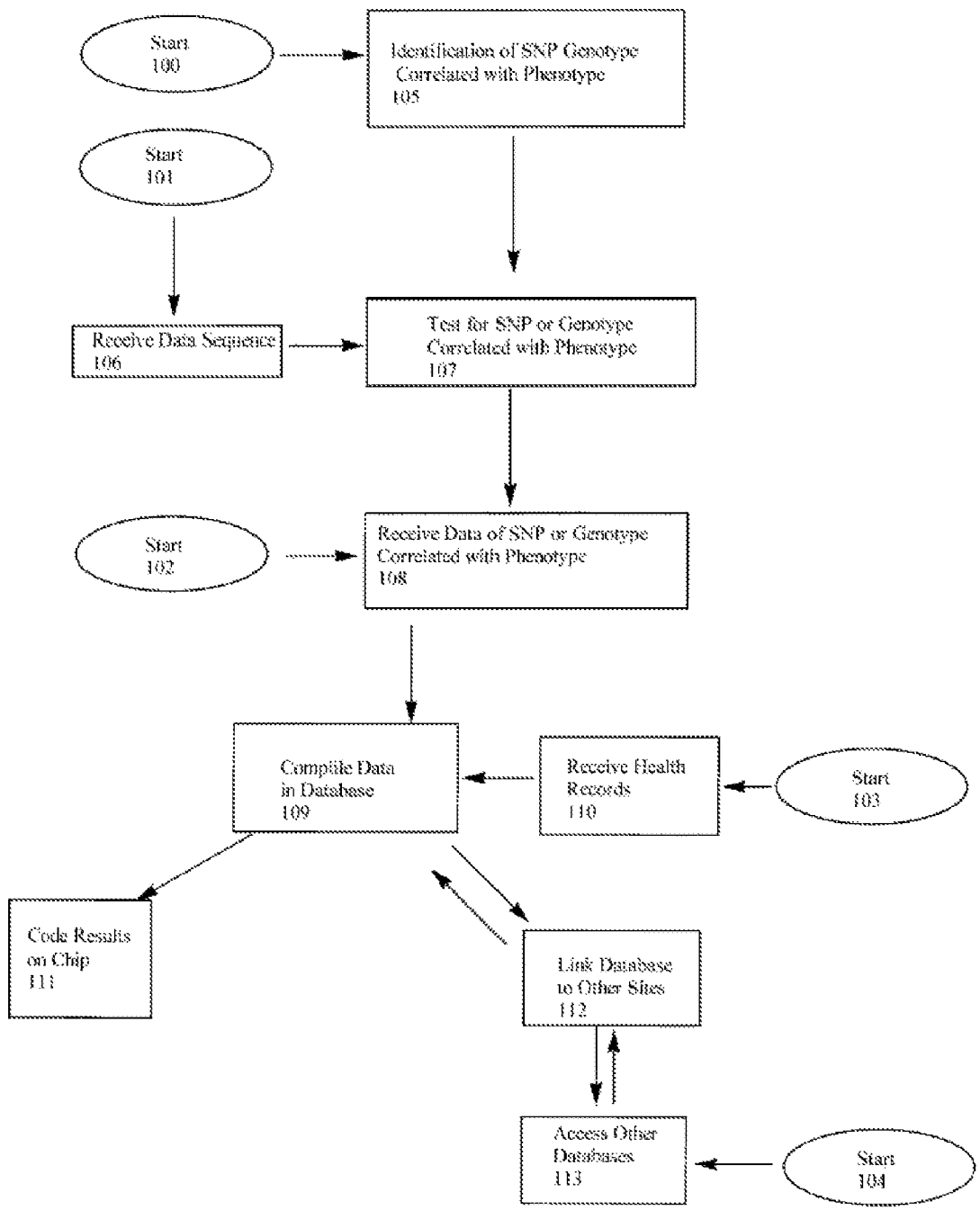
FIG. 23 illustrates a flow chart of the input of data and the output of results from the analysis and the correlation of the data pertaining to the breeding, veterinarian histories, and performance requirements of a group of animals.

FIG. 23 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have similar polymorphism in residual feed intake ("RFT") associated genes comprising:

(a) determining the genotype of each animal to be sub-grouped by determining the presence of single nucleotide polymorphisms in the RFI genes, and (b) segregating individual animals into sub-groups wherein each animal in a sub-group has similar polymorphisms in the RFI genes.

2. A method for sub-grouping animals according to genotype wherein the animals of each sub-group have similar genotypes in the RFI genes comprising:

(a) determining the genotype of each animal to be sub-grouped by determining the presence of single nucleotide polymorphisms of interest in the RFI genes, (b) segregating individual animals into sub-groups depending on whether the animals have, or do not have, the single nucleotide polymorphism(s) of interest in the RFI genes.

3. The method of paragraphs 1 or 2, wherein the single nucleotide polymorphism(s) of interest is selected from the group, wherein the single nucleotide polymorphism(s) of interest is selected from the group consisting of the nucleotide substitutions defined in SEQ ID NO 1 through SEQ ID NO 13 (FIG. 1 through FIG. 13)

4. A method for sub-grouping animals according to genotype wherein the animals of each sub-group have a similar genotype in the RFI genes comprising:

(a) determining the genotype of each animal to be sub-grouped by determining the presence of a nucleotide substitutions defined in SEQ ID NO 1 through SEQ ID NO 13 (FIG. 1 through FIG. 13).

(b) segregating individual animals into sub-groups depending on whether the animals have, or do not have nucleotide substitution(s) defined as defined in SEQ ID NO 1 through SEQ ID NO 13 (FIG. 1 through FIG. 13).

5. A method for identifying an animal having a desirable phenotype as compared to the general population of animals of that species, comprising determining the presence of a single nucleotide polymorphism(s) in the RFI genes of the animal, wherein the polymorphism is selected from the group comprising the nucleotide substitutions defined in SEQ ID NO 1 through SEQ ID NO 13 (FIG. 1 through FIG. 13)

6. The method of paragraph 5, wherein the desirable phenotype is feed intake, growth rate, body weight, carcass merit and composition, milk yield or any combination thereof.

7. The method of paragraph 5 or 6, wherein the desirable phenotype is birth weight (kg), gradefat (mm), lean meat yield (%), quality grade, ultrasound backfat (mm), ultrasound LM area (cm$^2$), ultrasound marbling or any combination thereof.

8. The method of any one of paragraphs 1 to 7 wherein the animal is a bovine.

9. The method of any one of paragraphs 1 to 8 wherein the RFI genes are bovine RFI genes.

10. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

11. The method according to paragraph 10, wherein the computer system is an interactive system whereby modifications to the output of the computer-assisted method may be correlated according to the input from the interactive device.

12. The method according to paragraph 10 or 11, further comprising the steps of inputting into the programmed computer diagnostic data related to the health of the cow or herd of cows; and correlating the diagnostic data to the breeding and veterinary histories of the cow or herd of cows.

13. The method according to any one of paragraphs 10 to 12, wherein the veterinary data comprises a vaccination record for a cow or herd of cows.

14. The method according to any one of paragraphs 10 to 13 wherein the health data is selected from the group consisting of husbandry condition data, herd history, and food safety data.

15. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

16. The method according to any one of paragraphs 10 to 15, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

17. The computer-assisted method according to any one of paragraphs 10 to 16 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

18. A method of transmitting data comprising transmission of information from such methods according to any one of paragraphs 10 to 16, selected from the group consisting of telecommunication, telephone, video conference, mass communication, a presentation, a computer presentation, a POWERPOINT™ presentation, internet, email, and documentary communication.

19. An interactive computer system according to any one of paragraphs 10 to 16 for tracking breeding and welfare histories of cows comprising breeding and veterinarian data corresponding to a bovine or herd of bovines, and wherein the computer system is configured to allow the operator thereof to exchange data with the device or a remote database.

20. The interactive computer system according to paragraph 19, wherein the input and output devices are a personal digital assistant or a pocket computer.

21. A method of doing business for tracking breeding and welfare histories of livestock comprising breeding and veterinarian data corresponding to one or more livestock animals comprising providing to a user the computer system of paragraph 19.

22. A method of doing business for tracking breeding and welfare histories of livestock comprising breeding and veterinarian data corresponding to one or more livestock animals comprising providing to a user the computer system of paragraph 20.

23. The method of doing business according to paragraph 21, further comprising providing the animal owner or customer with sample collection equipment, such as swabs and tags useful for collecting samples from which genetic data may be obtained, and wherein the tags are optionally packaged in a container which is encoded with identifying indicia.

24. The method of doing business according any one of paragraphs 10 to 16, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

25. The method of any one of paragraphs 8 to 24 wherein the data comprises presence or absence of one or more of a single nucleotide polymorphism(s) of interest in the RFI gene(s).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal as having a lower dry matter intake (DMI) as compared to a general population of bovine animals, comprising the steps of:
   (a) obtaining a biological sample from said bovine animal wherein the sample comprises nucleic acids;
   (b) detecting in said nucleic acids a homozygous Cytosine (C) at position 101 of SEQ ID No. 4 and a homozygous Guanine (G) at position 101 of SEQ ID No. 5; and
   (c) identifying said bovine animal as having a lower DMI when (b) is detected.

2. A method for identifying a bovine animal as having a lower Residual Feed Intake (RFI) as compared to a general population of bovine animals, comprising the steps of:
   (a) obtaining a biological sample from said bovine animal, wherein the sample comprises nucleic acids;
   (b) detecting in said nucleic acids a homozygous Cytosine (C) at position 101 of SEQ ID No. 4 and a homozygous Guanine (G) at position 101 of SEQ ID No. 5; and
   (c) identifying said bovine animal as having a lower RFI when (b) is detected.

3. A method for producing a population of bovine animals having a higher number of offspring a lower dry matter intake (DMI) as compared to a general population of bovine animals, comprising the steps of:
   (a) obtaining a biological sample from each bovine animal from a general population of bovine animals, wherein the sample comprises nucleic acids;
   (b) detecting in said nucleic acids a Cytosine (C) at position 101 of SEQ ID No. 4 and a Guanine (G) at position 101 of SEQ ID No. 5;
   (c) segregating individual bovine animals into sub-groups depending on whether the animals have, or do not have, a C at position 101 of SEQ ID No. 4 and a G at position 101 of SEQ ID No. 5; and
   (d) continuously breeding only animals that have a C at position 101 of SEQ ID No. 4 and a G at position 101 of SEQ ID No. 5, thereby producing the population of bovine animals.

* * * * *

SEQUENCE LISTING

```
<160> NUMBER OF SEQ ID NOS: 13

<210> SEQ ID NO 1
<211> LENGTH: 201
<212> TYPE: DNA
<213> ORGANISM: Bos sp.

<400> SEQUENCE: 1
ggggctctgt ggcaggtcgg gtgaaatgag tgcggctgag actccacgcc ctgcagcacg      60
gggctctgta gcaggtcagg actctggagt tgatccccca rcaccgccac gtgcaccccc     120
tttcctcagg tcatcgacaa gagcaagcga gacccctcgg aagagattga aattcttctg     180
cggtacgggc agcaccccaa c                                                201

<210> SEQ ID NO 2
<211> LENGTH: 201
<212> TYPE: DNA
<213> ORGANISM: Bos sp.

<400> SEQUENCE: 2
ggctctcagc tctcccatgt gtcatttcta acttcccata aaagcccttg gcagagcgga      60
tttcagtcgc tcgaggggga tattcaggtt caagaaatag maagcttata cgtaaatact     120
tgtaaataaa aaagcttata aacacattaa atgaacccaa tggacagagc ccctttcctg     180
ccctgggaag gcagacgcag t                                                201

<210> SEQ ID NO 3
<211> LENGTH: 201
<212> TYPE: DNA
<213> ORGANISM: Bos sp.

<400> SEQUENCE: 3
cagtgatgca gtggagtttc tgctttggag tcattcctgt ctacatttga attcttactc      60
aatatattac taagctgtct gacttttgcc aacacacctc kcgagcctca gtatcctcat     120
ctgtcagata ggggcataat gcctacttca tgatattgtg gtgagaatta catgagataa     180
cagatgaatc ctggattatc c                                                201
```

```
<210> SEQ ID NO 4
<211> LENGTH: 201
<212> TYPE: DNA
<213> ORGANISM: Bos sp.

<400> SEQUENCE: 4
attttaaact actttgttta gaaaagagtg gttagggttt tgtagcactt cctttgttca        60
tttttgcctc actaataaca cctagactca tactttggcc ycagcagtac agaggataca       120
ggtattgttt tctttaaaaa aaaaaacaaa aaacaaaaaa cagtcccatt tgaaagagaa       180
acaatggtgg tattgctctt t                                                 201

<210> SEQ ID NO 5
<211> LENGTH: 201
<212> TYPE: DNA
<213> ORGANISM: Bos sp.

<400> SEQUENCE: 5
aagtgagacc agagcgcgcc cgacgatgcg gtggctgtag tggtgaagct cccaagttga        60
gcttttctcg gcggttgttg ggcagctttg cagatgggaa rttatcagcc tcttagcagc       120
cctgagctgc cgtggcgcgg ggatttgggg aggaaaggac cgcaggcaga agctctctcc       180
cgacctgcag ccttgactgt t                                                 201

<210> SEQ ID NO 6
<211> LENGTH: 201
<212> TYPE: DNA
<213> ORGANISM: Bos sp.

<400> SEQUENCE: 6
aatcactttc agtaattatc tgaatagatc ttatggataa cttgctgccg cttctacatc        60
agcaggtgtt gtttcatctt gcacttttgt gttaatgggg rtattttctt tttgaaagcc       120
ttatgaatca aactctccta gcttccagct ttaaattaga attaaagagt taggaccatg       180
ctctgggtca ggccttggct t                                                 201

<210> SEQ ID NO 7
<211> LENGTH: 201
<212> TYPE: DNA
<213> ORGANISM: Bos sp.

<400> SEQUENCE: 7
tttgtgtgtc tgtgtgtgtg ttgttttgttt cattttagtt aaaaggagaa atgttatttt       60
ctatattgat gagctttggt ttgagcaagg aagagatgaa sgttcctagg agctgtgggt       120
cttcaataat ggatacagtc gacaggagta cttttctctgc ctgagtaaca gagaacccat      180
gatgactgag tagttcagaa a                                                 201

<210> SEQ ID NO 8
<211> LENGTH: 201
<212> TYPE: DNA
<213> ORGANISM: Bos sp.

<400> SEQUENCE: 8
taaggtcaat ggaaactgcc tgtgctatgt aggggcagta ctacccaggg gatgagaaat        60
cagccctgga gtcagatgta tccagtttta attccagctc wgttctctac taggtgagca       120
aacttgggca agctactata gtcactgaac ctcaacttcc ctctcttgaa aatgggtata      180
aaaactgtac ctgctagggg a                                                 201
```

```
<210> SEQ ID NO 9
<211> LENGTH: 201
<212> TYPE: DNA
<213> ORGANISM: Bos sp.

<400> SEQUENCE: 9
accaattggc attaacaagt gtgataggta tttgaaaaat tgttggcaaa acaactttct      60
tggaagacag aacaaaagaa ttaggaggtt tagaagtcag rcaacttcta atatcttata    120
ccattgacag tgatttgttc ctgtcatagc tcttctctga cctgttagtg aaggacaaaa    180
ttctaaaaaa atgtttagtc a                                              201

<210> SEQ ID NO 10
<211> LENGTH: 201
<212> TYPE: DNA
<213> ORGANISM: Bos sp.

<400> SEQUENCE: 10
tttccaagct gtgatagctt attattctga ttccctatgt accaactatt ctgcttgatg     60
gtctctttgt aattcttccc ttttgcagta ttttggtttt raatttctct tcttagaagt    120
ttgggtgaac tctctgctgg atggcaaact ccttgaatgt aggggtttgc tttaatgctt    180
ccttaattag accagagctt g                                              201

<210> SEQ ID NO 11
<211> LENGTH: 970
<212> TYPE: DNA
<213> ORGANISM: Bos sp.
<220> FEATURE:
<221> NAME/KEY: modified_base
<222> LOCATION: (473)..(475)
<223> OTHER INFORMATION: a, c, g, t, unknown, or other
<220> FEATURE:
<221> NAME/KEY: modified_base
<222> LOCATION: (480)..(481)
<223> OTHER INFORMATION: a, c, g, t, unknown, or other
<220> FEATURE:
<221> NAME/KEY: modified_base
<222> LOCATION: (483)..(485)
<223> OTHER INFORMATION: a, c, g, t, unknown, or other
<220> FEATURE:
<221> NAME/KEY: modified_base
<222> LOCATION: (489)
<223> OTHER INFORMATION: a, c, g, t, unknown, or other
<220> FEATURE:
<221> NAME/KEY: modified_base
<222> LOCATION: (496)..(497)
<223> OTHER INFORMATION: a, c, g, t, unknown, or other

<400> SEQUENCE: 11
ccgctacaac ctggcagccc tggccttggc ccccggagc cggctggacg ccttcgatta      60
cgactggtac aacgtctctg atcaggtggg cattcgacac atctgccgcc tccccagtag    120
ctgtggctcc tggcccccag ctggcctggg tccggtctgg gggccgcatt ggcatgactg    180
cagatcggca cagcccctgc ctccccacag gcggacctg tgaacgacct ggggaacaaa    240
ggctacctgg tgtttggcct catcctcttt gtgtgggagc tgctgcccac caccctgctg    300
gtgggcttct tccgggtaca tcggcccccg caggacctg tgagggccag tggagagggg    360
cggcactggc ggtccctggg ctgggttctg ggggtgtggg aggccagtgg ggggcagaag    420
raagcatcaa tggtggctcc cttccctaga gcaccagccg catcctcaac atnnnttttn    480
ntnnntggng tttttnnntgt gttgtaattt ggggttggaa aggatggtta atttttttgtg    540 aaaagactta ttctcagggg tgttatcata gcgtttgaaa ccacaagatt gattgtgggc    600
tcaaccttga aaaggttacg gttttttcca aaaaatgaac ttggccacca aatccgtgag    660
```

-continued

```
caaaaggggg gcccacctttt tggcatgaca taaaggaggc attttggggg ggaacctttt      720
gtccaaaagg ggggagcccc caaacgaatt caaagaactg ccccctgggt ttttaagtgg      780
taaccggatc caaaacaatt gacctccttc ccggggggcg gagaaaaaca gtaggccaca      840
ataaccctgg gggggattg ccacatgggg aaatggagat ttgagggggc ccttttgcta      900
atgaggaaac ctggcactcc cacaagttaa cctataatga tagggggtagg gaggcaagag    960 ggattttaag                                                              970

<210> SEQ ID NO 12
<211> LENGTH: 201
<212> TYPE: DNA
<213> ORGANISM: Bos sp.

<400> SEQUENCE: 12
caagaagatg cagttgaagg aggaagccag acagcccttc cccagcacag caagagaggt       60
tcggacaatg gacttatcta gagaaaaagg aggaggtcag ygggatcttg ggagaggggg     120
ttgagaagtt gggtcacttc tggggatgtg gccaaggacg agggaccaag gtgctcatgg     180
gtgctcaccc ttgggtacca c                                                201

<210> SEQ ID NO 13
<211> LENGTH: 201
<212> TYPE: DNA
<213> ORGANISM: Bos sp.

<400> SEQUENCE: 13
tcccaggtca agcaaaggcc atggcacagg atcttcaact ctaaatgctt gttgaattaa       60
aacgagttga aggaagtgca gagggagcag ctgtaggcag rtcaaaagag gtttgggaga    120
agcaaggaaa tatgaatgtt gaggttggtg acactgatta ggagcattca taggaattca    180
gaaccttcta gaccatcccc c                                                201
```